US006264641B1

(12) United States Patent
Van Gompel et al.

(10) Patent No.: US 6,264,641 B1
(45) Date of Patent: Jul. 24, 2001

(54) EXPANDABLE COVER GARMENT

(75) Inventors: Paul Theodore Van Gompel, Hortonville; Yung Hsiang Huang, Appleton; Jacqueline Ann Martin, Neenah, all of WI (US); Larry Neal Johns, New Milford, CT (US); Gary Mack Reynolds, Woodstock, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/249,434

(22) Filed: Feb. 12, 1999

Related U.S. Application Data

(60) Provisional application No. 60/084,515, filed on May 7, 1998, now abandoned, and provisional application No. 60/109,239, filed on Nov. 19, 1998, now abandoned.

(51) Int. Cl.[7] .................................................. A61F 13/20

(52) U.S. Cl. ................ 604/385.22; 604/378; 604/385.01

(58) Field of Search ............................ 604/378, 386, 604/385.01, 385.101, 385.22

(56) References Cited

U.S. PATENT DOCUMENTS

| Re. 33,106 | 11/1989 | Beckestrom | 604/385.2 |
|---|---|---|---|
| 3,776,233 | 12/1973 | Schaar | 128/287 |
| 3,885,568 | 5/1975 | Schaar | 128/287 |

(List continued on next page.)

FOREIGN PATENT DOCUMENTS

| 0 669 855 | 6/1996 | (AU) . | |
|---|---|---|---|
| 0 217 032 A3 | 4/1987 | (EP) . | |
| 0 567 792 A1 | 11/1993 | (EP) | A61F/13/15 |

(List continued on next page.)

OTHER PUBLICATIONS

American Society for Testing Materials (ASTM) Designation: D 5169–91, "Standard Test Method for Shear Strength (Dymanic Method) of Hook and Loop Touch Fasteners," pp. 687–689, published Nov. 1991.

American Society for Testing Materials (ASTM) Designation: D 5170–91, "Standard Test Method for Peel Strength ("T" Method) of Hook and Loop Touch Fasteners," pp. 690–692, published Nov. 1991.

(List continued on next page.)

Primary Examiner—Richard K. Seidel
Assistant Examiner—Cris Rodriguez
(74) Attorney, Agent, or Firm—Paul Yee

(57) ABSTRACT

An integral absorbent article has a longitudinal article length and a lateral article width. The article includes an absorbent composite having first and second longitudinally opposed end regions, laterally opposed side regions, a bodyside surface, an outward surface, and a first longitudinally terminal end edge. The absorbent composite further includes a substantially liquid-impermeable backsheet layer; a liquid permeable topsheet layer; and a retention portion sandwiched between said backsheet and topsheet layers. An extensible outercover is joined to extend over a major portion of said outward surface of the said absorbent composite. The extensible outercover is desirably capable of providing a the selected elongation when subjected to a tensile force. The extensible outercover is also desirably capable of providing a selected, sustained deformation, when subjected to an applied tensile force and then allowed to relax after a removal of the applied force. In particular aspects, the outercover can provide an elongation of at least about 1 cm when subjected to a tensile force of 30 gmf per inch. In further aspects, the extensible outercover may also provide a substantially permanent deformation of at least about 20%, when subjected to a tensile force of 50 gmf per inch and then allowed to relax for a period of 1 minute (after a removal of the applied tensile force).

26 Claims, 21 Drawing Sheets

U.S. PATENT DOCUMENTS

| | | | |
|---|---|---|---|
| 3,901,236 | 8/1975 | Assarsson et al. | 128/284 |
| 3,920,018 | 11/1975 | Schaar | 128/287 |
| 3,978,861 | 9/1976 | Schaar | 128/287 |
| 4,076,663 | 2/1978 | Masuda et al. | 260/17.5 GC |
| 4,081,301 | 3/1978 | Buell | 156/164 |
| 4,249,532 | 2/1981 | Polansky et al. | 128/287 |
| 4,286,082 | 8/1981 | Tsubakimoto et al. | 526/240 |
| 4,341,216 | 7/1982 | Obenour | 128/287 |
| 4,534,769 | 8/1985 | De Jonckheere et al. | 604/369 |
| 4,595,441 | 6/1986 | Holvoet et al. | 156/265 |
| 4,663,220 | 5/1987 | Wisneski et al. | 428/221 |
| 4,666,542 | 5/1987 | De Jonckheere | 156/164 |
| 4,687,477 | 8/1987 | Suzuki et al. | 604/385 A |
| 4,699,620 | 10/1987 | Bernardin | 604/385 A |
| 4,699,823 | 10/1987 | Kellenberger et al. | 428/219 |
| 4,701,172 | 10/1987 | Stevens | 604/385 A |
| 4,701,173 | 10/1987 | Zehner et al. | 604/385 A |
| 4,701,174 * | 10/1987 | Dobrin | 604/385 A |
| 4,701,175 | 10/1987 | Boland et al. | 604/385 A |
| 4,704,116 | 11/1987 | Enloe | 604/385 A |
| 4,710,187 | 12/1987 | Boland et al. | 604/385 A |
| 4,731,066 | 3/1988 | Korpman | 604/366 |
| 4,738,677 | 4/1988 | Foreman | 604/385 R |
| 4,747,846 * | 5/1988 | Boland et al. | 604/38 A |
| 4,753,646 | 6/1988 | Enloe | 604/385 R |
| 4,756,709 * | 7/1988 | Stevens | 604/385 A |
| 4,762,582 | 8/1988 | de Jonckheere | 156/164 |
| 4,834,738 * | 5/1989 | Kielpikowski et al. | 604/385.2 |
| 4,846,825 * | 7/1989 | Enloe et al. | 604/385.1 |
| 4,850,990 * | 7/1989 | Huntoon et al. | 604/385.2 |
| 4,883,480 | 11/1989 | Huffman et al. | 604/385.1 |
| 4,916,005 | 4/1990 | Lippert et al. | 428/192 |
| 4,936,840 * | 6/1990 | Proxmire | 604/385.2 |
| 4,938,753 | 7/1990 | Van Gompel et al. | 604/385.2 |
| 4,938,754 | 7/1990 | Mesek | 604/385.2 |
| 4,938,755 | 7/1990 | Foreman | 604/385.2 |
| 4,950,262 | 8/1990 | Takagi | 604/385.1 |
| 4,965,122 | 10/1990 | Morman | 428/225 |
| 5,019,066 | 5/1991 | Freeland et al. | 604/385.2 |
| 5,019,073 | 5/1991 | Roessler et al. | 604/391 |
| 5,026,364 | 6/1991 | Robertson | 604/385.1 |
| 5,034,007 | 7/1991 | Igaue et al. | 604/365 |
| 5,037,416 | 8/1991 | Allen et al. | 604/385.1 |
| 5,098,423 | 3/1992 | Pieniak et al. | 604/385.1 |
| 5,133,707 | 7/1992 | Rogers et al. | 604/389 |
| 5,226,992 | 7/1993 | Morman | 156/62.4 |
| 5,263,948 | 11/1993 | Karami et al. | 604/383 |
| 5,263,949 | 11/1993 | Karami et al. | 604/383 |
| 5,269,775 | 12/1993 | Freeland et al. | 604/385.2 |
| 5,304,159 | 4/1994 | Tanji et al. | |
| 5,360,422 | 11/1994 | Brownlee et al. | |
| 5,399,219 | 3/1995 | Roessler et al. | 156/259 |
| 5,486,166 | 1/1996 | Bishop et al. | 604/366 |
| 5,490,846 | 2/1996 | Ellis et al. | 604/366 |
| 5,527,303 | 6/1996 | Milby, Jr. et al. | 604/385.1 |
| 5,531,730 | 7/1996 | Dreier | 604/385.2 |
| 5,540,671 * | 7/1996 | Dreier | 604/385.2 |
| 5,540,796 | 7/1996 | Fries | 156/164 |
| 5,542,942 | 8/1996 | Kline et al. | 604/385.2 |
| 5,558,660 * | 9/1996 | Dreier | 604/385.2 |
| 5,558,661 | 9/1996 | Roe et al. | 604/385.2 |
| 5,562,650 | 10/1996 | Everett et al. | 604/378 |
| 5,571,096 | 11/1996 | Dobrin et al. | 604/385.2 |
| 5,580,411 | 12/1996 | Nease et al. | 156/260 |
| 5,593,401 | 1/1997 | Sosalla et al. | 604/385.2 |
| 5,595,618 | 1/1997 | Fries et al. | 156/164 |
| 5,605,735 | 2/1997 | Zehner et al. | 428/100 |
| 5,624,422 * | 4/1997 | Allen | 604/385.1 |
| 5,624,429 | 4/1997 | Long et al. | 604/391 |
| 5,628,737 | 5/1997 | Dobrin et al. | 604/383 |
| 5,643,242 | 7/1997 | Lavon et al. | |
| 5,836,932 * | 11/1998 | Buell et al. | 604/396 |
| 5,843,066 * | 12/1998 | Dobrin | 604/385.1 |
| 5,853,403 * | 12/1998 | Tanzer et al. | 604/385.1 |
| 5,895,379 * | 4/1999 | Litchholt et al. | 604/378 |
| 5,897,547 * | 4/1999 | Schmitz | 604/391 |
| 5,947,948 * | 9/1999 | Roe et al. | 604/385.2 |
| 6,129,720 * | 10/2000 | Blenke et al. | 604/385.16 |
| B1 4,636,207 | 11/1989 | Buell | 604/370 |
| B1 4,662,875 | 4/1989 | Hirotsu et al. | 604/389 |

FOREIGN PATENT DOCUMENTS

| | | | |
|---|---|---|---|
| 0 591 647 A2 | 4/1994 | (EP) | A61F/13/15 |
| 0 604 764 A1 | 7/1994 | (EP) | |
| 2 680 316 A1 | 2/1993 | (FR) | |
| 2 284 741 A | 6/1996 | (GB) | |
| 2 297 474 B | 8/1996 | (GB) | |
| 2 297 491 A | 8/1996 | (GB) | |
| 8 402 274 | 2/1985 | (NL) | |
| WO 88/06008 A1 | 8/1988 | (WO) | |
| WO 93/03698 A1 | 3/1993 | (WO) | |
| WO 94/28844 A2 | 12/1994 | (WO) | |
| WO 95/02384 A1 | 1/1995 | (WO) | |
| WO 96/19166 A1 | 6/1996 | (WO) | |
| WO 96/22064 A1 | 7/1996 | (WO) | |
| WO 96/23466 A1 | 8/1996 | (WO) | |
| WO 96/31179 A2 | 10/1996 | (WO) | |
| WO 96/32083 A1 | 10/1996 | (WO) | |
| WO 97/00056 A1 | 1/1997 | (WO) | |
| WO 97/14385 A1 | 4/1997 | (WO) | |
| WO 97/24094 A1 | 7/1997 | (WO) | |
| WO 97/24283 A1 | 7/1997 | (WO) | |
| WO 97/26850 A1 | 7/1997 | (WO) | A61F/13/15 |
| WO 97/46185 A1 | 12/1997 | (WO) | |
| WO 98/33465 A1 | 8/1998 | (WO) | |
| 92/6027 | 8/1992 | (ZA) | |

OTHER PUBLICATIONS

American Society for Testing Materials (ASTM) Designation: D 882–95a, "Standard Test Method for Tensile Properties of Thin Plastic Sheeting," pp. 182–187, published Dec. 1995.

Federal Test Nethod Standard (FTMS) No. 191A, Method 5514, "Water Resistance of Cloth; Low Range, Hydrostatic Pressure Method," Jul. 20. 1978, 3 pages.

TAPPI Official Test Method T 543 om–94, "Bending Resistance of Paper (Gurley Type Tester)," published by the TAPPI Press, Atlanta, Georgia, pp. 1–7.

* cited by examiner

EXPANDABLE COVER GARMENT

This application claims priority from presently U.S. Provisional Application No. 60/084,515 filed on May 7, 1998 now abandoned and presently U. S. Provisional Application No. 60/109,239 and filed on Nov. 19, 1998, now abandoned.

FILED OF THE INVENTION

The present invention relates to garment articles. More particularly, the present invention relates to absorbent articles, desirably disposable absorbent articles, which have a distinctive, extensible outercover.

BACKGROUND OF THE INVENTION

Conventional garment articles, such as disposable diapers and other disposable absorbent articles, have typically employed adhesive or mechanical fasteners which attach appointed waistband sections of the articles around a wearer. In addition, various configurations of waist elastics, leg elastics, elasticized liners, and elasticized outercovers have been employed on garment articles to help produce and maintain the fit of the articles about the body contours of the wearer.

Other conventional absorbent garments have included folded pleats in the outercover. The pleats are arranged to expand open as the garment absorbs liquids.

The external surfaces of such disposable absorbent products may include a nonwoven fibrous material or a matte-finished film material. In some arrangements, pattern embossments have been formed into outer surface of the outercover to provide a decorative pattern.

Still other disposable garments have incorporated an absorbent composite jointed to an outercover composed of elastomeric materials, such as elastomeric, stretch-bonded-laminate materials. Such materials have included a layer meltblown elastomeric fibers which has been stretched and sandwiched between facing layers composed of a polypropylene spunbond nonwoven fabric. The meltblown layer has typically been pattern-bonded to the facing layers with thermal bonds, sonic bonds and/or adhesive bonds.

Conventional garment articles, such as those described above, have not provided desired levels of fit, absorbency, resistance to leakage, low cost and ease of manufacture. As a result, there has been a continued need for garments having improvements in such properties.

BRIEF DESCRIPTION OF THE INVENTION

Generally stated, the present invention provides an integral absorbent article having a longitudinal article length and a lateral article width. The article includes an absorbent composite having first and second longitudinally opposed end regions, laterally opposed side regions, a bodyside surface, an outward surface, and a first longitudinally terminal end edge. The absorbent composite further includes a substantially liquid-impermeable backsheet layer; a liquid permeable topsheet layer, and a retention portion sandwiched between said backsheet and topsheet layers. An extensible outercover is joined to extend over a major portion of said outward surface of said absorbent composite. The extensible outercover is desirably capable of providing a selected elongation when subjected to an applied tensile force. The extensible outercover is also desirably capable of providing a selected, sustained deformation, when subjected to an applied tensile force and then allowed to relax after the tensile force has been removed.

In particular arrangements, the extensible outercover can be substantially non-elastomeric. In other configurations, the absorbent article can include an expandable attachment section joined along at least a portion of each side region of the absorbent composite in the first end region of the absorbent composite. Each expandable attachment section can be expandable at least outwardly, and each expandable attachment section is configured to secure its correspondingly joined side edge region of the absorbent composite to the outward surface of the first body panel.

By incorporating its various aspects, the article of the present invention can provide an article having improved fit, improved absorbency and improved resistance to leakage. The article can also be produced at lower cost and with greater efficiency. In addition, the article of the invention can also provide improved breathability, greater softness, and more cloth-like properties.

BRIEF DESCRIPTION OF THE INVENTION

The present invention will be more fully understood and further advantages will become apparent when reference is made to the following detailed description of the invention and the drawings, in which:

FIG. 1 representatively shows a partially cut-away, top plan view of the inward surface of an example of an article of the invention;

FIG. 1A representatively shows a schematic, expanded, lateral cross-sectional view taken with respect to the line 1A—1A of FIG. 1;

FIG. 1B representatively shows a schematic, expanded, lateral cross-sectional view taken with respect to the line 1B—1B of FIG. 1;

FIG. 1C representatively shows a schematic, expanded, lateral cross-sectional view taken with respect to the line 1C—1C of FIG. 1;

FIG. 1D representatively shows a schematic, expanded, longitudinal cross-sectional view taken with respect to the line 1D—1D of FIG. 1;

FIG. 1E representatively shows a plan view of the outward surface of the garment illustrated in FIG. 1;

FIG. 2 representatively shows a partially cut-away, top plan view of the inward surface of another example of an article of the invention which has a shortened absorbent back-sheet;

FIG. 2A representatively shows a schematic, expanded, lateral cross-sectional view taken with respect to the line 2A—2A of FIG. 2;

FIG. 2B representatively shows a schematic, expanded, lateral cross-sectional view taken with respect to the line 2B—2B of FIG. 2;

FIG. 2C representatively shows a schematic, expanded, lateral cross-sectional view taken with respect to the line 2C—2C of FIG. 2;

FIG. 2D representatively shows a schematic, expanded, longitudinal cross-sectional view taken with respect to the line 2D—2D of FIG. 2;

FIG. 2E representatively shows a schematic, expanded, lateral cross-sectional view of a configuration where the backsheet layer of the absorbent composite has longitudinally extending pleats which allow a significant cross-directional extension of the backsheet layer;

FIG. 3 representatively shows a partially cut-away, top plan view of the inward surface of an article of the invention having an absorbent composite attached to front and back body panels, where the absorbent composite has a pleated topsheet layer and a pleated backsheet layer;

FIG. 3A representatively shows a schematic, expanded, lateral cross-sectional view taken with respect to the line 3A—3A of FIG. 3;

FIG. 3B representatively shows a schematic, expanded, lateral cross-sectional view taken with respect to the line 3B—3B of FIG. 3;

FIG. 3C representatively shows a schematic, expanded, lateral cross-sectional view taken with respect to the line 3C—3C of FIG. 3;

FIG. 3D representatively shows a schematic, expanded, longitudinal cross-sectional view taken with respect to the line 3D—3D of FIG. 3;

FIG. 4 representatively shows a top plan view of an outward side of an article of the invention which includes a patterned attachment substantially affixes a selected region of the extensible outercover to an underlying portion of the article;

FIG. 4A representatively shows a schematic, expanded, lateral cross-sectional view along line 4A—4A of FIG. 4;

FIG. 5 representatively shows a schematic, expanded, lateral cross-sectional view of an absorbent composite affixed to the outward side of a body panel with expandable attachment sections provided by pleated side margins of the absorbent composite;

FIG. 5A representatively shows a schematic, expanded, lateral cross-sectional view of an absorbent composite affixed to the outward side of a body panel with expandable attachment sections provided by an expandable topsheet layer and pleated side margins of the backsheet layer;

FIG. 5B representatively shows a schematic, expanded, lateral cross-sectional view of an absorbent composite affixed to the outward side of a body panel with expandable attachment sections provided by an expandable topsheet layer and another configuration of pleated side margins of the backsheet layer, FIG. 6 representatively shows a schematic, expanded, lateral cross-sectional view of an absorbent composite affixed to the outward side of a body panel with expandable attachment sections provided by a separately provided expandable element;

FIG. 7 representatively shows a schematic, expanded, lateral cross-sectional view of an absorbent composite affixed to the outward side of a body panel with expandable attachment sections provided by the side margins of an expandable topsheet layer and an expandable backsheet layer, FIG. 7A representatively shows a schematic, expanded, lateral cross-sectional view of an absorbent composite having a non-pleated, non-expandable backsheet layer where the absorbent composite is affixed to the outward side of a body panel with expandable attachment sections provided by side margins of an expandable topsheet layer;

FIG. 7B representatives shows a schematic, expanded, lateral cross-sectional view of an absorbent composite having a non-pleated, non-expandable topsheet layer where the absorbent composite is affixed to the outward side of a body panel with expandable attachment sections provided by the side margins of an expandable backsheet layer;

FIG. 8 shows a representative stress-strain curve provided by a necked spun-bond fabric web material;

FIG. 9 representatively shows a schematic, expanded, lateral cross-sectional view of an expandable cover which is substantially unattached to an adjacent substrate;

FIG. 9A representatively shows a schematic, expanded, lateral cross-sectional view of an expandable cover which is attached to an elastomeric substrate;

FIG. 9B representatively shows a schematic, expanded, lateral cross-sectional view of an expandable cover which is attached to a non-elastomeric, substantially non-expandable substrate;

DETAILED DESCRIPTION OF THE INVENTION

Figure 1:
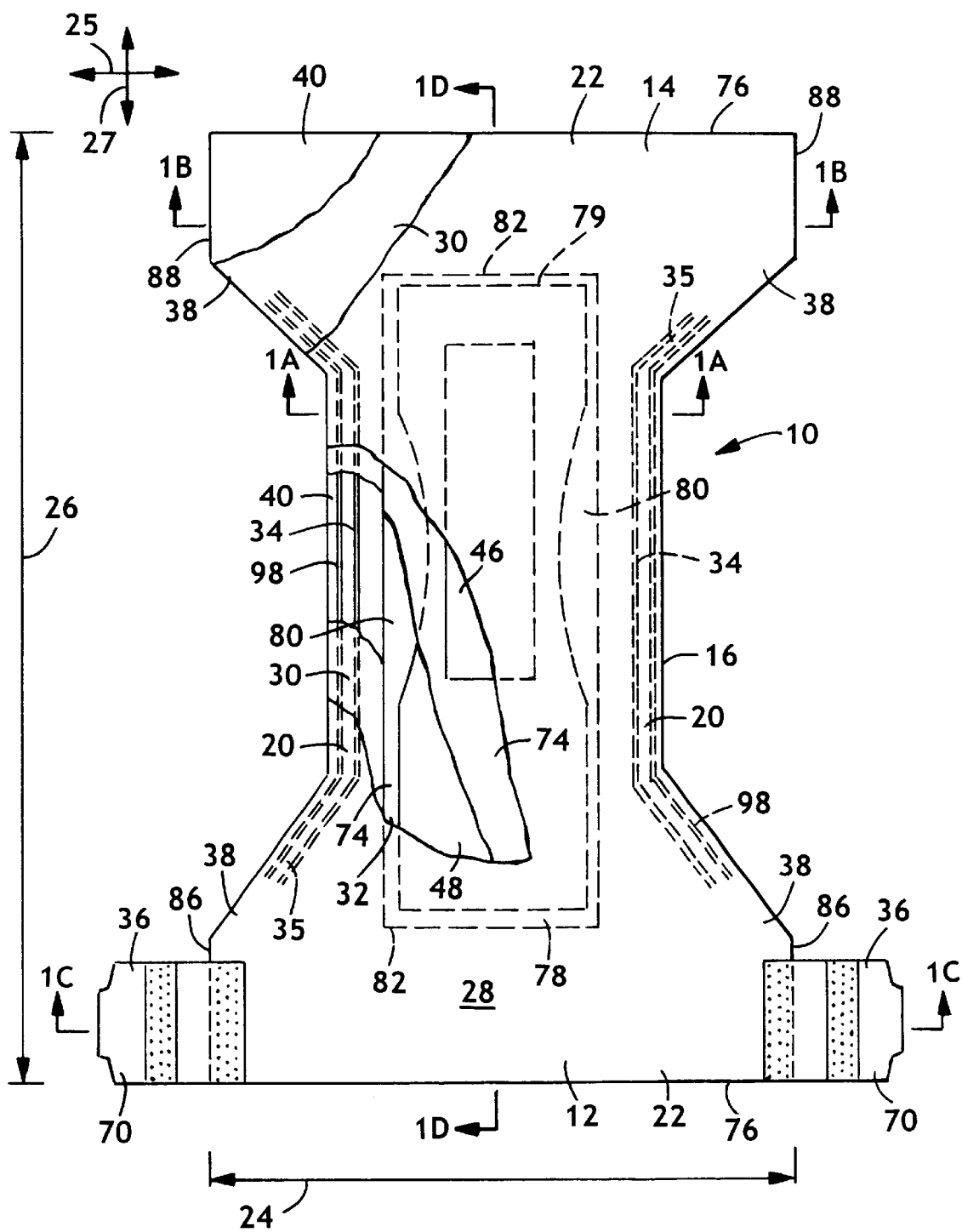
Figure 1A:
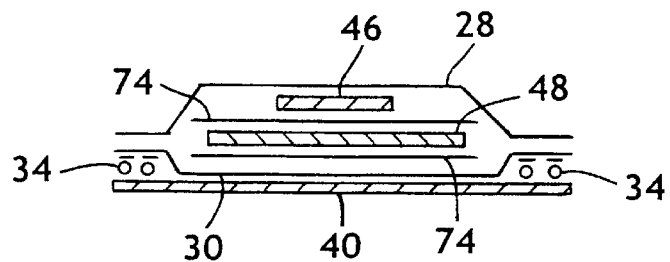

The various aspects and embodiments of the invention will be described in the context of a disposable absorbent article, such as a disposable diaper. It is, however, readily apparent that the present invention could also be employed with other articles, such as caps, gowns, shoe covers, feminine care articles, children's training pants, incontinence garments and the like. Typically, the disposable articles are intended for limited use and are not intended to be laundered or otherwise cleaned for reuse. A disposable diaper, for example, is discarded after it has become soiled by the wearer. Optionally, a disposable diaper may include a single-use, absorbent insert, and a limited-use outercover which may be reused several times.

It should also be noted that, when employed in the present disclosure, the terms "comprises", "comprising" and other derivatives from the root term "comprise" are intended to be open-ended terms that specify the presence of any stated features, elements, integers, steps, or components, but do not preclude the presence or addition of one or more other features, elements, integers, steps, components, or groups thereof. Accordingly, such terms are intended to be synonymous with the words "has", "have", "having", "includes", "including" and any derivatives of these words.

With reference to FIGS. 1 through 4A an article, such as the representatively shown integral absorbent article provided by the example diaper 10, has a longitudinal article length 26 along a longitudinal direction 27, and an article width 24 along a lateral, transverse cross-direction 25. The article includes an absorbent composite 32 which has first and second longitudinally opposed end regions 78 and 79, and has laterally opposed side regions 80. The absorbent composite also includes an appointed outward surface, an opposed bodyside surface, and first and second longitudinally terminal end edges 82. Additionally, the absorbent composite 32 includes a substantially liquid-impermeable backsheet layer 30, a substantially liquid permeable topsheet layer 28, and a retention portion 48 which is sandwiched between the backsheet and topsheet layers. As illustrated, the backsheet layer can be configured to provide the outward surface of the absorbent composite, and the topsheet layer can be configured to provide the bodyside surface of the absorbent composite. An extensible outercover 40 is joined to extend over a major portion of the outward surface of the absorbent composite 32. The extensible outercover is desirably capable of providing a selected elongation when subjected to an applied tensile force. The extensible outercover is also desirably capable of providing a selected, sustained deformation, when subjected to an applied tensile force and then allowed to relax for a selected time period after removing the applied tensile force. The measurement of the selected time period begins immediately after the removal of the tensile force. Desirably, the sustained deformation is a substantially permanent deformation. The selected elongation and sustained deformation can occur at least along the lateral cross-direction 25 of the article. Optionally, the selected elongation and sustained deformation can occur along the longitudinal direction 27 of the article, or may occur along both the cross-direction and longitudinal direction of the article.

In particular aspects, the extensible outercover can provide an elongation of at least about 1 cm when subjected to a tensile force of 30 gmf per inch (per 2.54 cm). The extensible outercover can also provide a substantially permanent deformation of at least about 20%, when subjected to a tensile force of 50 gmf per inch (per 2.54 cm) and then allowed to relax, after a removal of the tensile force, for a period of 1 minute.

As representatively shown, the article can have a first waistband portion 12 positioned at the back or rear of the diaper, and a second or front waistband portion 14 positioned longitudinally opposite of the first waistband portion 12. An intermediate, crotch portion 16 interconnects the first and second waistband portion 12 and 14, respectively. In the shown configurations, the intermediate portion is operatively provided by the absorbent composite 32. A fastening system, such as a system including fasteners 36, is configured to provide a back-to-front fastening in which the back waistband portion 12 can be arranged in an overlapping relation with the front waistband portion 14 to thereby encircle the wearer's body and hold the diaper secure on the wearer during use. Optionally, the fastening system can employ fastener tabs 36 which are configured to provide a front-to-back fastening which arranges and joins the front waistband portion 14 in an overlapping relation with the back waistband portions 12 to thereby encircle the wearer's body during use.

In further aspects of the invention, the extensible outercover 40 can be substantially non-elastomeric. Accordingly, the extensible outercover does not have the stretch and retraction characteristics of natural rubber. In other aspects, the absorbent article can include an expandable attachment section 90 (e.g. FIG. 3A) joined along at least a portion of each side region 80 of the absorbent composite 32 in the first end region 78 and/or second end region 79 of the absorbent composite. Each expandable attachment section 90 can be expandable at least outwardly or at least along the cross-direction 25 of said article, and each expandable attachment section is configured to secure its correspondingly joined side edge region of the absorbent composite to the outward surface 56 of its corresponding body panel 52 or 53.

Figure 9:
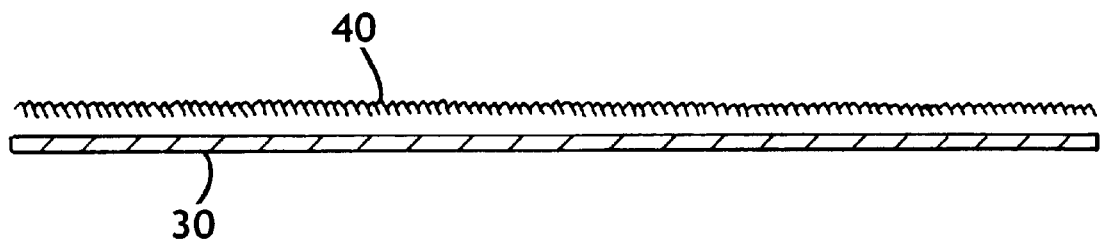

The article of the invention incorporates a distinctive, separately provided extensible outercover 40 which includes an extensible fabric layer which is operatively attached or otherwise joined to extend over a major portion of the outward surface of the article. In particular, the extensible outercover 40 can extend over a major portion of the outward surface of the absorbent composite 32. Desirably, the extensible outercover can extend over substantially an entire area of the outward surface of the absorbent composite. The selected extensibility in the outercover can allow the outercover to accommodate and cooperate with the properties of the other materials or components to which the extensible outercover is attached in the article. In regions where the outercover is not affixed to the article (e.g. FIG. 9), the extensible outercover can be free to advantageously expand with minimal force and with a high amount of permanent deformation.

Extensible regions in the outercover 40 are provided in areas where the outercover is not directly affixed to the article. In the article of the invention, the extensible regions can desirably be located over the regions of the absorbent composite which are appointed for expansion during the absorption of liquids. For example, the absorbent composite can expand outwardly during use, and the outercover can elongate and extend in correspondence with the expansion of the absorbent composite and/or other components of the article. In desired aspects, the outercover 40 can be extensible along the transverse lateral direction 25. In optional aspects, the outercover can be extensible along the longitudinal direction 27, or along a combination of both the lateral and longitudinal directions.

Figure 9A:
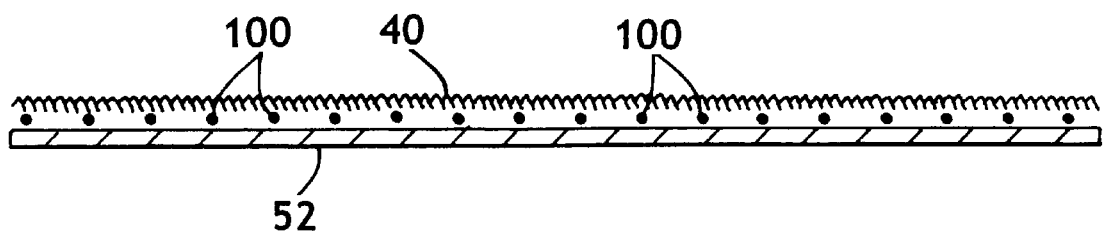

Elasticized regions in the outercover 40 can be created where the extensible outercover is affixed to an elastomeric component. For example, an elastomeric region in the outercover 40 can be created where the extensible outercover is affixed to an elastomerically stretchable body panel 52 (e.g. FIG. 9A). Substantially non-extensible regions in the outercover can be created where the extensible outercover 40 is affixed to a substantially non-extensible component. For example, a substantially non-extensible region in the outercover 40 can be created where the extensible outercover 40 is affixed to a substantially non-extensible component, such as a substantially non-extensible substrate layer of the article.

Figure 4:
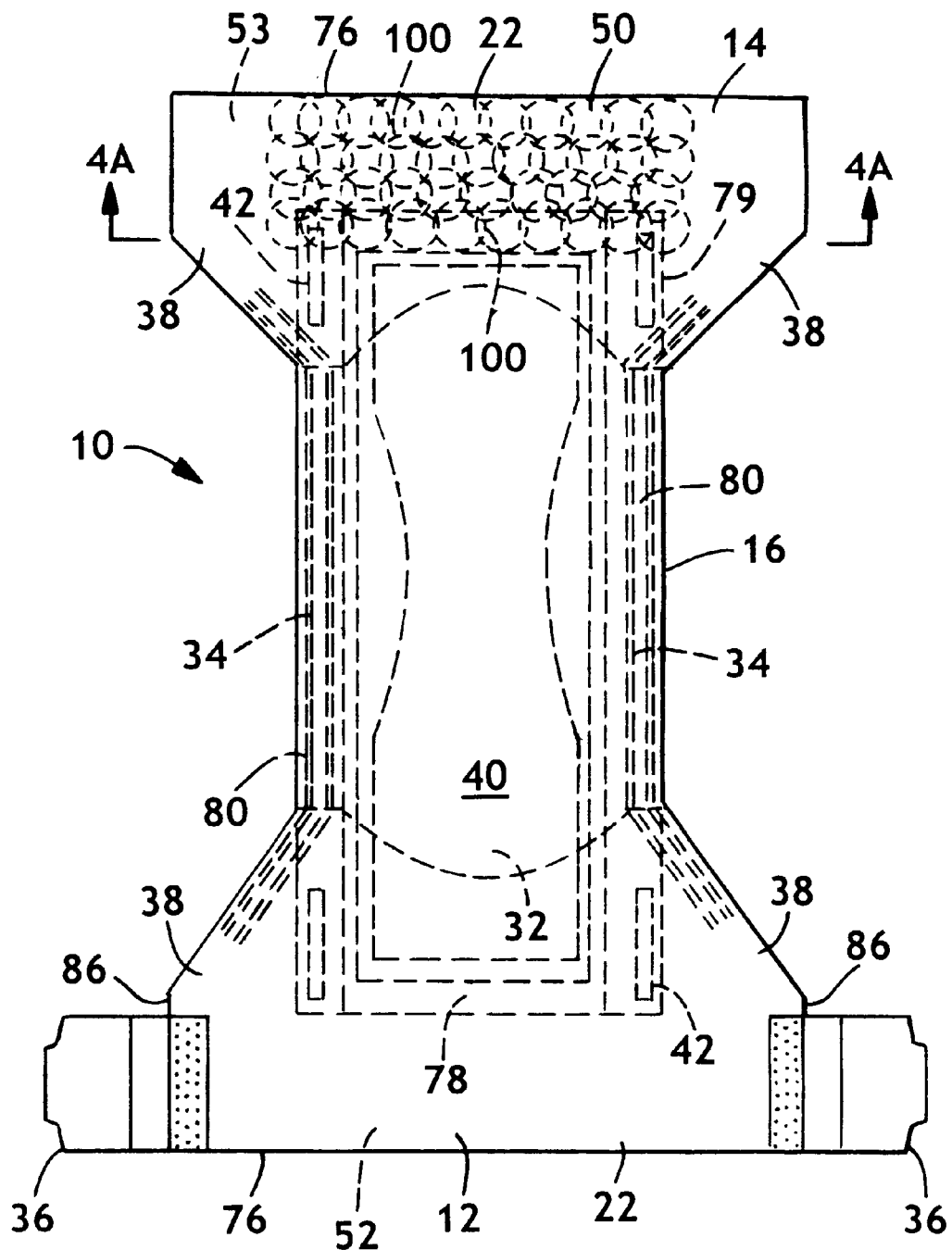
Figure 4A:
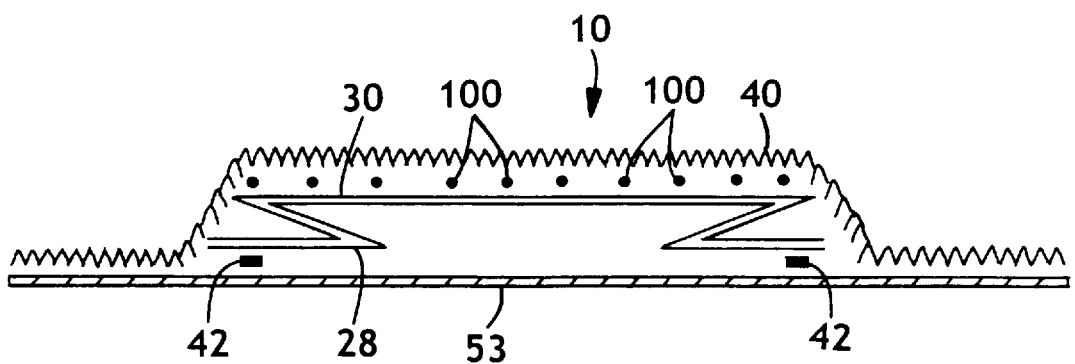
Figure 5:
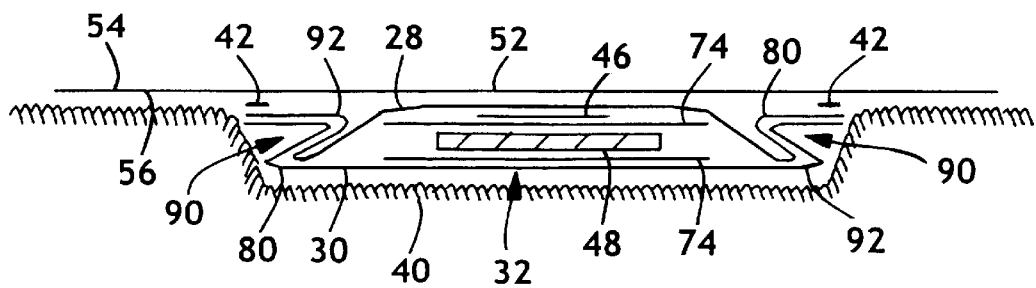
Figure 5A:
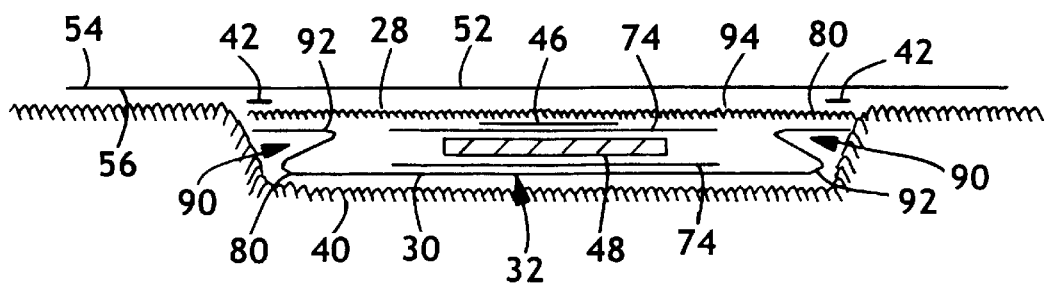
Figure 5B:
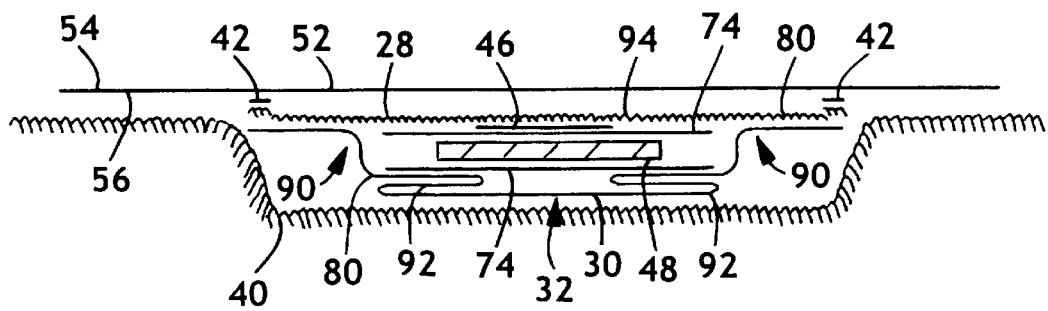
Figure 9B:
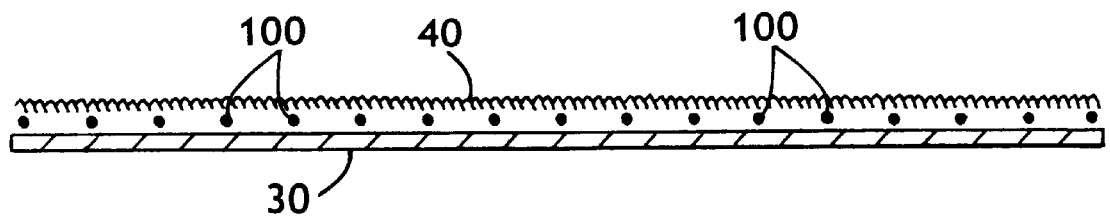

In particular configurations, the substantially non-extensible regions of the outercover member 40 can be constructed by affixing the extensible nonwoven fabric of the outercover to a substantially non-extensible component, such as a substantially non-extensible backsheet layer (e.g. FIG. 9B). With reference to FIGS. 4 and 4A, for example, the resultant non-extensible region can provide a landing zone region 50 which is composed of an integral portion of the nonwoven fabric of the extensible outercover. The backsheet layer 30 of the absorbent composite 32 can, for example, be composed of a substantially non-extensible polymer film, and the nonwoven fabric of the extensible outercover 40 can be adhesively attached or otherwise affixed to the front waistband region of the backsheet layer with a selected, substantially non-extendible attachment 100. The attachment 100 may be irregularly or randomly distributed, or may be arranged in a predetermined, pattern array, such as the representatively shown swirl pattern. The nonwoven fabric can thereby provide a complementary component of an interengaging mechanical fastening system. For example, the affixed portion of the outercover in the landing zone 50 can provide a female loop component of a mechanical hook-and-loop fastening system. The affixing of the extensible outercover material to the polymer film can prevent the necked fabric from excessively elongating and extending in the lateral direction during the ordinary operation of the fastening system.

In particular aspects, the extensible outercover 40 can be capable of providing an elongation of at least a minimum of about 1 cm when subjected to a tensile force of 30 gmf per inch (0.116 Newtons per cm) of cross-wise length ("width") of a test sample. Alternatively, the extensible outercover can provide an elongation of at least about 3 cm, and optionally, can provide an elongation of at least about 5 cm to provide improved performance. In other aspects, the extensible outercover 40 can be capable of providing an elongation of not more than a maximum of about 30 cm when subjected to the tensile force of 30 gmf per inch (0.116 N per cm) of cross-wise length ("width") of a test sample. Alternatively, the extensible outercover can provide an elongation of not more than about 20 cm, and optionally, can provide an elongation of not more than about 10 cm to provide further improved performance.

In further aspects, the extensible outercover can be capable of providing a substantially permanent deformation of at least a minimum of about 20% when subjected to a tensile force of 50 gmf per inch (0.193 Newtons per cm) of cross-wise length of the test sample, and then allowed to relax (after a removal of the applied tensile force) for a period of 1 minute. Alternatively, the extensible outercover can provide a substantially permanent deformation of at least about 20%, and optionally, can provide a substantially permanent deformation of at least about 30% to provide improved benefits. In still other aspects, the extensible outercover can provide a substantially permanent deformation of not more than a minimum of about 60% when subjected to the tensile force of 50 gmf per inch (0.193 N/cm) of cross-wise length of the test sample, and then allowed to relax for a period of 1 minute after a removal of the applied tensile force. Alternatively, the extensible outercover can provide a substantially permanent deformation of not more than about 50%, and optionally, can provide a substantially permanent deformation of not more than about 40% to provide further improved benefits. It should be readily appreciated that the described removal of the applied force results in a zero applied tensile stress and a zero applied tensile force.

It should be noted that the elongation, extension or permanent deformation properties of the outercover are determined when the outercover is dry. Additionally, the percentage of elongation, extension or permanent deformation can be determined in accordance with the following formula: $100*(L-L_o)/(L_o)$;
where: L=elongated length, and $L_o$=initial length.

The extensible outercover member can be composed of various materials. For example, the extensible outercover can be composed of a necked fabric, a creped fabric, a micro-pleated fabric, polymer films or the like, as well as combinations thereof. The fabrics may be woven or nonwoven materials, such as spunbond fabrics.

An example of a suitable extensible outercover material is a 60% necked, polypropylene spunbond having a basis weight of about 1.2 osy. The necked spunbond material had the physical properties representatively shown in the stress-strain curve set forth in FIG. 8. The properties of the spunbond material were determined with respect to a 2 inch wide sample having 3 inches of sample length spanning between an initial 3 inch separation of the holding jaws of a conventional set of tensile testing equipment.

Examples of suitable manufacturing techniques and suitable necked nonwoven fabric materials are described in U.S. Pat. No. 4,965,122 entitled REVERSIBLE NECKED MATERIAL AND PROCESS TO MAKE IT, by M. T. Morman which was issued Oct. 23, 1990. The entire disclosure of this document is incorporated herein by reference in a manner that is consistent herewith.

For the purposes of the present disclosure, the term "% necked" or "percent neckdown" refers to a ratio or percentage determined by measuring the difference between the pre-necked dimension and the necked dimension of a neckable material, and then dividing that difference by the pre-necked dimension of the neckable material. The percentage of necking (percent neck) can be determined in accordance with the description in the above-mentioned U.S. Pat. No. 4,965,122 entitled REVERSIBLE NECKED MATERIAL AND PROCESS TO MAKE IT, by M. T. Morman which was issued Oct. 23, 1990.

The necked nonwoven fabric can be configured to be substantially non-extensible in a selected region of the outercover member 40. For example, the necked nonwoven fabric be employed to construct an improved fastener landing zone 50 which includes the necked spunbond fabric layer. More particularly, the backsheet layer 30 of the absorbent composite 32 can be composed of a substantially non-extensible polymer film, and the necked spunbond fabric of the extensible outercover 40 can be adhesively attached to the front waistband region of the backsheet layer. The necked spunbond fabric can thereby provide the appointed, female loop component of a mechanical hook-and-loop fastening system, wherein the adhesive attachment to the non-extensible polymer film can prevent the necked spunbond from laterally elongating and extending during the ordinary operation of the fastening system.

The necked spunbond fabric can also provide a very cloth-like feel to the outercover 40. The necked fabric is desirably air-permeable, and breathability regions can be created where the extensible outercover material is attached to overlie a breathable component which is positioned on the bodyside of the outercover. For example, the extensible cover 40 can be attached to overlie a front body panel 52 composed of an air-permeable SMS (spunbond-meltblown-spunbond) laminate material. Since the SMS front body panel and the attached, necked spunbond fabric are both breathable, the overall composite of the necked spunbond and SMS materials can remain breathable.

As representatively shown, the front waistband section 14 of the diaper 10 has a laterally opposed, front pair of side edge regions 88, and the rear waistband section 12 has a laterally opposed, rear pair of side edge regions 86. The intermediate section 16 interconnects the front and rear waistband section and provides a diaper crotch region which is typically positioned between the legs of the wearer. The article has an appointed fastener landing member 50 which is disposed on the outward surface of the article. In the example representatively shown in FIG. 1E, for example, the landing member 50 can be disposed on the outward surface of the backsheet layer 30. The liquid permeable topsheet layer 28 is superposed in facing relation with the backsheet layer 30, and the retention portion 48 is operably connected and affixed between the backsheet layer 30 and topsheet layer 28, In desired arrangements, the topsheet layer 28 and the retention portion 48 can be constructed to be substantially nonelastomeric and can be operatively attached to the backsheet member 30 to substantially restrain excessive stretching of the backsheet member.

FIGS. 1, 1E, 2, 3 and 4 show typical plan views of the representative disposable diaper 10 in its generally flat-out, uncontracted state (i.e., with substantially all elastic induced gathering and contraction removed), and show the bodyside surface of the diaper, which is intended to contact the wearer, facing the viewer. The outer edges of the diaper define a periphery 18 with laterally opposed, longitudinally extending side edge margins 20; and longitudinally opposed, laterally extending end edge margins 22. The side edges define leg openings for the diaper, and optionally, are curvilinear and contoured. The end edges are shown as straight, but optionally, may be curvilinear.

With regard to the designated surfaces of the article and components, the various inward surfaces are configured to face toward the body of the wearer when the article is placed about the wearer. The various outward surfaces are configured to face away from the wearer's body when the article is placed about the wearer.

The diaper 10 typically includes a porous, liquid permeable topsheet 28; a substantially liquid impermeable backsheet 30; a retention portion 48 positioned and connected between the topsheet and backsheet; a surge management portion 46 located operatively adjacent to the retention portion; and a system of elastomeric gathering members, such as a system including leg elastics 34 and optional waist elastics (not shown). The surge management portion 46 is positioned in a liquid communication with the retention portion 48 of the absorbent structure, and the topsheet 28, backsheet 30, retention portion 48, surge management portion 46, leg elastic members 34 and the waist elastics may be assembled together into a variety of well-known diaper configurations. The diaper can additionally include a system of containment flaps (not shown), and/or a system of separately provided side panels or members which form ear regions 38 of the article.

The containment flaps and/or side panels may be elasticized or otherwise rendered elastomeric.

Examples of articles which include elasticized side panels and selectively configured fastener tabs are described in U.S. patent application Ser. No. 168,615 of T. Roessler et al., entitled DYNAMIC FITTING DIAPER, and filed Dec. 16, 1993 Various techniques for forming the desired fastening systems are described in U.S. Pat. No. 5,399,219 of T. Roessler et al., entitled METHOD FOR MAKING A FASTENING SYSTEM FOR A DYNAMIC FITTING DIAPER and issued Mar. 21, 1995 in U.S. patent application Ser. No. 286,086 of D. Fries, entitled A PROCESS FOR ASSEMBLING ELASTICIZED EAR PORTIONS and filed Aug. 3, 1994 which issued as U.S. Pat. No. 5,540,796: and in U.S. patent application Ser. No. 08/1415,383 of D. Fries, entitled AN ASSEMBLY PROCESS FOR A LAMINATED TAPE and filed Apr. 3, 1995 which issued as U.S. Pat. No. 5,595,618. The disclosures of the above-described documents are incorporated herein by reference in a manner that is consistent (not in conflict) herewith.

Diaper 10 generally defines the longitudinally extending length dimension 26 and the laterally extending width dimension 24, as representatively shown in FIG. 1. The diaper may have any desired shape, such as rectangular, I-shaped, a generally hour glass shape, or a T-shape. With the T-shape, the crossbar of the "T" may comprise the front waistband portion of the diaper, or may alternatively comprise the rear waistband portion of the diaper.

The topsheet 28 and backsheet 30 may be generally coextensive, and optionally, may be non-coextensive. Either or both of the topsheet 28 and backsheet 30 may have length and width dimensions which are generally larger than and extend beyond the corresponding dimensions of the retention portion 48 to provide the end edge margins or regions 78 and 79, and the side edge margins or regions 80 of the absorbent composite 32. In particular aspects, the side edge margins of the absorbent composite can be configured to provide at least a portion of the side margins 20 of the article. The topsheet 28 is operatively associated with and superimposed on backsheet 30, thereby defining the periphery of the diaper.

The waistband regions comprise those portions of the diaper, which when worn, wholly or partially cover or encircle the waist or mid-lower torso of the wearer. The intermediate, crotch region 16 lies between and interconnects the waistband regions 14 and 12, and comprises that portion of the diaper which, when worn, is positioned between the legs of the wearer and covers the lower torso of the wearer. Thus, the intermediate crotch region 16 is an area where repeated liquid surges typically occur in the diaper or other disposable absorbent article.

The backsheet 30 can typically be located along an outer-side surface of the absorbent composite 32 and may be composed of a liquid permeable material, but desirably comprises a material which is configured to be substantially impermeable to liquids. For example, a typical backsheet can be manufactured from a thin plastic film, or other flexible, substantially liquid-impermeable material. As used in the present specification, the term "flexible" refers to materials which are compliant and which will readily conform to the general shape and contours of the wearer's body. The backsheet 30 prevents the exudates contained in the absorbent composite 32 from wetting articles, such as bedsheets and overgarments, which contact diaper 10. In particular embodiments of the invention, the backsheet 30 can include a film, such as a polyethylene film, having a thickness of from about 0.012 millimeters (0.5 mil) to about 0.051 millimeters (2.0 mils). For example, the backsheet film can have a thickness of about 1.25 mil.

Alternative constructions of the backsheet may comprise a woven or nonwoven fibrous web layer which has been totally or partially constructed or treated to impart the desired levels of liquid impermeability to selected regions that are adjacent or proximate the absorbent composite. For example, the backsheet may include a gas-permeable, nonwoven fabric layer laminated to a polymer film layer which may or may not be gas-permeable. Other examples of fibrous, cloth-like backsheet materials can comprise a stretch thinned or stretch thermal laminate material composed of a 0.6 mil (0.015 mm) thick polypropylene cast film and a 0.7 ounce per square yard (23.8 gsm) polypropylene spunbond material (2 denier fibers). A material of this type has been employed to form the outercover of a HUGGIES ULTRATRIM diaper, which has been commercially available from Kimberly-Clark Corporation. The backsheet 30 typically provides the outercover of the article. Optionally, however, the article may include a separate outercover component member which is additional to the backsheet.

Backsheet 30 may include a microporous, "breathable" material which permits gases, such as water vapor, to escape from the absorbent composite 32 while substantially preventing liquid exudates from passing through the backsheet. For example, the breathable backsheet may be composed of a microporous polymer film or a nonwoven fabric which has been coated or otherwise modified to impart a desired level of liquid impermeability. For example, a suitable microporous film can be a PMP-1 material, which is available from Mitsui Toatsu Chemicals, Inc., a company having offices in Tokyo, Japan; or an XKO-8044 polyolefin film available from 3M Company of Minneapolis, Minn. The backsheet may also be embossed or otherwise provided with a pattern or matte finish to exhibit a more aesthetically pleasing appearance.

In the various configurations of the invention, where a component, such as the backsheet 30 or the containment flaps are configured to be permeable to gas while having a resistance and limited permeability to aqueous liquid, the liquid resistant component can have a construction which is capable of supporting a selected hydrohead of water substantially without leakage therethrough. A suitable technique for determining the resistance of a material to liquid penetration is Federal Test Method Standard FTMS 191 Method 5514, 1978, or an equivalent thereof.

The backsheet member 30 is sufficiently impermeable liquid and semi-liquid materials to substantially prevent the undesired leakage of waste materials, such as urine and feces.

For example, the backsheet member can desirably support a hydrohead of at least about 45 centimeters (cm) substantially without leakage. The backsheet member 30 can alternatively support a hydrohead of at least about 55 cm, and optionally, can support a hydrohead of at least about 60 cm, or more, to provide improved benefits.

The size of the backsheet 30 is typically determined by the size of absorbent composite 32 and the particular diaper design selected. Backsheet 30, for example, may have a generally T-shape, a generally I-shape or a modified hourglass shape, and may extend beyond the terminal edges of absorbent composite 32 by a selected distance, such as a distance within the range of about 1.3 centimeters to 2.5 centimeters (about 0.5 to 1.0 inch), to provide at least a portion of the side and end margins.

The topsheet 28 presents a body-facing surface which is compliant, soft-feeling, and non-irritating to the wearer's skin. Further, the topsheet 28 can be less hydrophilic than absorbent composite 32, and is sufficiently porous to be liquid permeable, permitting liquid to readily penetrate through its thickness to reach the absorbent composite. A suitable topsheet layer 28 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The topsheet layer 28 is typically employed to help isolate the wearer's skin from liquids held in the absorbent composite 32.

Various woven and nonwoven fabrics can be used for topsheet 28. For example, the topsheet may be composed of a meltblown or spunbonded web of the desired fibers, and may also be a bonded-carded-web. The various fabrics can be composed of natural fibers, synthetic fibers or combinations thereof.

For the purposes of the present description, the term "nonwoven web" means a web of fibrous material which is formed without the aid of a textile weaving or knitting process. The term "fabrics" is used to refer to all of the woven, knitted and nonwoven fibrous webs.

The topsheet fabrics may be composed of a substantially hydrophobic material, and the hydrophobic material may optionally be treated with a surfactant or otherwise processed to impart a desired level of wettability and hydrophilicity. In a particular embodiment of the invention, topsheet 28 is a nonwoven, spunbond polypropylene fabric composed of about 2.8–3.2 denier fibers formed into a web having a basis weight of about 22 gsm and density of about 0.06 gm/cc. The fabric can be surface treated with an operative amount of surfactant, such as about 0.28% Triton X-102 surfactant. The surfactant can be applied by any conventional means, such as spraying, printing, brush coating or the like.

The topsheet 28 and backsheet 30 are connected or otherwise associated together in an operable manner. As used herein, the term "associated" encompasses configurations in which topsheet 28 is directly joined to backsheet 30 by affixing topsheet 28 directly to backsheet 30, and configurations wherein topsheet 28 is indirectly joined to backsheet 30 by affixing topsheet 28 to intermediate members which in turn are affixed to backsheet 30. Topsheet 28 and backsheet 30 can, for example, be joined to each other in at least a portion of the diaper periphery by attachment mechanisms (not shown) such as adhesive bonds, sonic bonds, thermal bonds, pinning, stitching or any other attachment techniques known in the art, as well as combinations thereof.

For example, a uniform continuous layer of adhesive, a patterned layer of adhesive, a prayed pattern of adhesive or an array of separate lines, swirls or spots of construction bonds may be used to affix the topsheet 28 to the backsheet 30. It should be readily appreciated that the above-described attachment mechanisms may also be employed to suitably interconnect, assemble and/or affix together the various other component parts of the articles which are described herein.

The absorbent body or composite 32 provides an absorbent structure which includes a retention portion 48 for holding and storing absorbed liquids and other waste materials, such as the shown absorbent pad composed of selected hydrophilic fibers and high-absorbency particles. The absorbent composite is positioned and sandwiched between the topsheet 28 and backsheet 30 to form the diaper 10. The absorbent composite has a construction which is generally compressible, conformable, non-irritating to the wearer's skin, and capable of absorbing and retaining body exudates. It should be understood that, for purposes of this invention, the absorbent composite structure may comprise a single, integral piece of material, or alternatively, may comprise a plurality of individual separate pieces of material which are operably assembled together.

Various types of wettable, hydrophilic fibrous material can be used to form the component parts of absorbent composite 32 particularly the retention portion 48. Examples of suitable fibers include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers; and synthetic fibers composed of a nonwettable thermoplastic polymer, such as polypropylene fibers, which have been hydrophilized by appropriate means. The fibers may be hydrophilized, for example, by treatment with silica, treatment with a material which has a suitable hydrophilic moiety and is not readily removable from the fiber, or by sheathing the nonwettable, hydrophobic fiber with a hydrophilic polymer during or after the formation of the fiber. For the purposes of the present invention, it is contemplated that selected blends of the various types of fibers mentioned above may also be employed.

As used herein, the term "hydrophilic" describes fibers or the surfaces of fibers which are wetted by the aqueous liquids in contact with the fibers.

The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with such system, fibers having contact angles less than 90° are designated "wettable", while fibers having contact angles greater than 90° are designated "nonwettable".

The absorbent composite structure 32 can comprise an absorbent body having a matrix of hydrophilic fibers, such as a web of cellulosic fluff, mixed with particles of high-absorbency material. In particular arrangements, the retention portion 48 of the absorbent composite 32 may comprise a mixture of superabsorbent hydrogel-forming particles and synthetic polymer meltblown fibers, or a mixture of superabsorbent particles with a fibrous coform material comprising a blend of natural fibers and/or synthetic polymer fibers. The superabsorbent particles may be substantially homogeneously mixed with the hydrophilic fibers, or may be non-uniformly mixed. For example, the concentrations of superabsorbent particles may be arranged in a non-step-wise gradient through a substantial portion of the thickness (z-direction) of the absorbent structure, with lower concentrations toward the bodyside of the absorbent composite and relatively higher concentrations toward the outside of the absorbent structure. Suitable z-gradient configurations are described in U.S. Pat. No. 4,699,823 issued Oct. 13, 1987 to Kellenberger et al., the entire disclosure of which is incorporated herein by reference in a manner that is consistent (not in conflict) with the present description. Alternatively, the concentrations of superabsorbent particles may be arranged in a non-step-wise gradient, through a substantial portion of the thickness (z-direction) of the absorbent structure, with higher concentrations toward the bodyside of the absorbent composite and relatively lower concentrations toward the outside of the absorbent structure. The superabsorbent particles may also be arranged in a generally discrete layer within the matrix of hydrophilic fibers. In addition, two or more different types of superabsorbent may be selectively positioned at different locations within or along the fiber matrix.

The high-absorbency material may comprise absorbent gelling materials, such as superabsorbents. Absorbent gelling materials can be natural, synthetic and modified natural polymers and materials. In addition, the absorbent gelling materials can be inorganic materials, such as silica gels, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations or Van der Waals forces.

Examples of synthetic absorbent gelling material polymers include the alkali metal and ammonium salts of poly (acrylic acid) and poly (methacrylic acid), poly (acrylamides), poly(vinyl ethers), maleic anhydride copolymers with vinyl ethers and alpha-olefins, poly(vinyl pyrrolidone), poly(vinylmorpholinone), poly(vinyl alcohol), and mixtures and copolymers thereof. Further polymers suitable for use in the absorbent composite include natural and modified natural polymers, such as hydrolyzed acrylonitrile-grafted starch, acrylic acid grafted starch, methyl cellulose, chitosan, carboxymethyl cellulose, hydroxypropyl cellulose, and the natural gums, such as alginates, xanthan gum, locust bean gum and the like. Mixtures of natural and wholly or partially synthetic absorbent polymers can also be useful in the present invention. Other suitable absorbent gelling materials are disclosed by Assarsson et al. in U.S. Pat. No. 3,901,236 issued Aug. 26, 1975. Processes for preparing synthetic absorbent gelling polymers are disclosed in U.S. Pat. No. 4,076,663 issued Feb. 28, 1978 to Masuda et al. and U.S. Pat. No. 4,286,082 issued Aug. 25, 1981 to Tsubakimoto et al.

Synthetic absorbent gelling materials typically are xerogels which form hydrogels when wetted. The term "hydrogel", however, has commonly been used to also refer to both the wetted and unwetted forms of the material.

As mentioned previously, the high-absorbency material used in the absorbent composite 32 is generally in the form of discrete particles. The particles can be of any desired shape, for example, spiral or semi-spiral, cubic, rod-like, polyhedral, etc. Shapes having a large greatest dimension/smallest dimension ratio, like needles, flakes, and fibers, are also contemplated for use herein. Conglomerates of particles of absorbent gelling material may also be used in absorbent composite 32. Desired for use are particles having an average size of from about 20 microns to about 1 millimeter. "Particle size" as used herein means the weighted average of the smallest dimension of the individual particles.

The hydrophilic fibers and high-absorbency particles can be configured to form an average composite basis weight which is within the range of about 400–900 gsm. in certain aspects of the invention, the average composite basis weight is within the range of about 500–800 gsm, and alternatively is within the range of about 550–750 gsm to provide desired performance.

To improve the containment of the high-absorbency material, absorbent composite structure 32 can include an overwrap, such as wrap sheet 74, which is placed immediately adjacent and around absorbent composite 32 and may be bonded to the absorbent structure and to the various other components of the article. The wrap sheet is preferably a layer of absorbent material which covers the major bodyside and outside surfaces of the absorbent composite, and preferably encloses substantially all of the peripheral edges of the absorbent composite to form a substantially complete envelope thereabout. Alternatively, the wrap sheet can provide an absorbent wrapping which covers the major bodyside and outside surfaces of the absorbent composite, and encloses substantially only the lateral side edges of the absorbent composite. Accordingly, both the linear and the inwardly curved portions of the lateral side edges of the wrap sheet would be closed about the absorbent composite. In such an arrangement, however, the end edges of the wrap sheet may not be completely closed around the end edges of the absorbent composite at the waistband regions of the article.

For example, the complete wrap sheet 74, or at least the bodyside layer of the wrap sheet, may comprise a meltblown web composed of meltblown fibers, such as meltblown polypropylene fibers. Another example of absorbent wrap 74 may comprise a low porosity cellulosic web, such as a tissue composed of an approximately 50/50 blend of hardwood/softwood fibers.

The absorbent wrap 74 may comprise a multi-element wrapsheet which includes a separate bodyside wrap layer and a separate outside wrap layer, each of which extends past all or some of the peripheral edges of absorbent composite 32. Such a configuration of the wrap sheet can, for example, facilitate the formation of a substantially complete sealing and closure around the peripheral edges of absorbent composite 32. In the back waistband portion of the illustrated diaper, the absorbent wrap may also be configured to extend an increased distance away from the periphery of the absorbent composite to add opacity and strength to the back side-sections of the diaper.

In the illustrated embodiment, the bodyside and outside layers of absorbent wrap 74 can extend at least about ½ inch beyond the peripheral edges of the absorbent composite to provide an outwardly protruding, flange-type bonding area over which the periphery of the bodyside portion of the absorbent wrap may be completely or partially connected to the periphery of the outside portion of the absorbent wrap.

The bodyside and outside layers of wrap sheet 74 may be composed of substantially the same material, or may be composed of different materials. For example, the outside layer of the wrap sheet may be composed of a relatively lower basis weight material having a relatively high porosity, such as a wet strength cellulosic tissue composed of softwood pulp. The bodyside layer of the wrap sheet may comprise one of the previously described wrap sheet materials which has a relatively low porosity. The low porosity bodyside layer can better prevent the migration of superabsorbent particles onto the wearers skin, and the high porosity, lower basis weight outerside layer can help reduce costs.

Diaper 10 can also include a surge management layer 46 which helps to decelerate and diffuse surges of liquid that may be introduced into the absorbent composite of the article. In the illustrated embodiment, for example, surge layer 46 can be located on an inwardly facing body side surface of topsheet layer 28. Alternatively, surge layer 46 may be located adjacent to an outer side surface of topsheet 28. Accordingly, the surge layer would then be interposed between topsheet 28 and absorbent composite 32. Examples of suitable surge management layers 46 are described in U.S. patent application Ser. No. 206,986 of C. Ellis and D. Bishop, entitled FIBROUS NONWOVEN WEB SURGE LAYER FOR PERSONAL CARE ABSORBENT ARTICLES AND THE LIKE, filed Mar. 4, 1994 which issued as U.S. Pat. No. 5,486,166; and U.S. patent application Ser. No. 206,069 of C. Ellis and R. Everett, entitled IMPROVED SURGE MANAGEMENT FIBROUS NONWOVEN WEB FOR PERSONAL CARE ABSORBENT ARTICLES AND THE LIKE, filed Mar. 4, 1994 which issued as U.S. Pat. No. 5,490,846; the entire disclosures of which are hereby incorporated by reference in a manner that is consistent herewith.

The article may include at least one body panel, such as the representatively shown first body panel 52, and may also include the shown second body panel 53. Each body panel has a body side surface 54, an outward surface 56, and a panel length 58 which is less than the article length 26. Each body panel also includes a first, outboard terminal end edge 60, and a second, relatively inboard terminal end edge 62. In desired configurations, the first, outboard terminal end edge 60 can be substantially coterminous with a first terminal end edge of the article.

With respect to the first body panel 52, for example, an expandable attachment section 90 is joined along at least a portion of each side region 80 of the absorbent composite 32 in the first end region 78 of the absorbent composite. Each expandable attachment section 90 can be expandable or otherwise extendible at least outwardly or at least along the article width 24, and each expandable attachment section is configured to secure its correspondingly joined side edge region of the absorbent composite to the outward surface 56 of the first body panel 52. Each expandable attachment section 90 is operatively interposed between the outward surface 56 of its correspondingly associated body panel 52 to allow an expansion movement of the absorbent composite outwardly away from the outward surface of the associated body panel. Similarly, with respect to the second body panel 53, a corresponding, expandable attachment section 90 may be joined between the second body panel along at least a portion of each side region 80 of the absorbent composite 32 in a second end region 79 of the absorbent composite.

In particular aspects of the invention, at least one of the backsheet and topsheet layers can provide a longitudinal component length 84 which is less than the article length 26, and the backsheet and topsheet layers may have unequal longitudinal lengths. The backsheet layer may be longer than the topsheet layer, or the topsheet layer may be longer than the backsheet layer. In particular configurations, the backsheet layer 30 may provide the component length 84 which is less than the article length 26, and in other arrangements, the topsheet layer 28 may provide the component length which is less than the article length 26. In a desired configuration representatively shown in FIGS. 2 and 3, each of the topsheet and backsheet layers have an associated, individual component length which is less than the overall article length. Accordingly, both of the topsheet and backsheet layers may provide longitudinal component lengths which are less than the article length.

The first body panel 52 is desirably a separately provided member which is attached to and extends across the inwardly facing, bodyside surface of the first end region 78 of the absorbent composite. The first body panel can be joined to the absorbent composite and arranged to provide the back waistband portion 12 of the article. Alternatively, the first body panel 52 may be joined to the absorbent composite and arranged to provide the front waistband portion 14 of the article. As representatively shown in FIG. 3, the first body panel 52 can be joined to provide the back waistband portion 12 of the article, and a second body panel 53 can be joined to a longitudinally opposed end of the absorbent composite 32 to provide the front waistband 14 of the article.

The second body panel 53 can be a separately provided member, which is attached to extend across the bodyside surface of the second end region 79 of the absorbent composite. The second body panel 53 has a longitudinal panel length 59 which is less than the article length 26, and the second body panel is longitudinally spaced away from the first body panel 52. In desired configurations, the second body panel 53 can have a longitudinally outboard terminal end edge 61 which is substantially coterminous with a second, terminal end edge of the article. The absorbent composite 32 is attached to extend across and span over an outward surface 56 of the second body panel 53, and as representatively shown, the absorbent composite can operatively extend to interconnect and span between the first and second body panels.

As representatively shown, a corresponding, expandable attachment section 90 can be joined along at least a portion of each associated side region 80 of the absorbent composite 32 in the second end region 79 of the absorbent composite. Each expandable attachment section 90 can be expandable at least along the lateral cross-direction of the article width 24, and each expandable attachment section can be configured to secure its correspondingly joined side edge region of the absorbent composite to the outward surface 56 of the second body panel 53.

Absorbent articles having an absorbent composite attached with expandable attachment sections to an outward surface of one or more body panels are described in co-pending U.S. patent application Ser. No. 09/250,470 entited A DISPOSABLE GARMENT HAVING DRYNESS BARRIERS WITH EXPANDABLE ATTACHMENT TO AN ABSORBENT by P. VanGompel et al., and filed Feb. 12, 1999. The entire disclosure of this document is incorporated herein by reference in a manner that is consistent herewith.

Each body panel can have a desired shape, which may be generally rectangular or non-rectangular. Laterally opposed end sections of the body panel can extend transversely beyond the side edges of the absorbent composite 32 to provide extending ear portions 38 of the article. Accordingly, each body panel can extend across substantially the entire cross-directional width of its corresponding waistband portion of the article. Each body panel can extend laterally beyond the side edges of the topsheet layer 28 and can extend laterally beyond the side edges of the backsheet layer 30. In particular arrangements, the body panel can be configured with lateral end sections which have a tapered shape to provide tapered ear portions. Each tapered ear portions can have a relatively longer longitudinal length adjacent the side margins of the absorbent composite, and a relatively shorter longitudinal length at the laterally distal ends of the ear portion.

Figure 3:
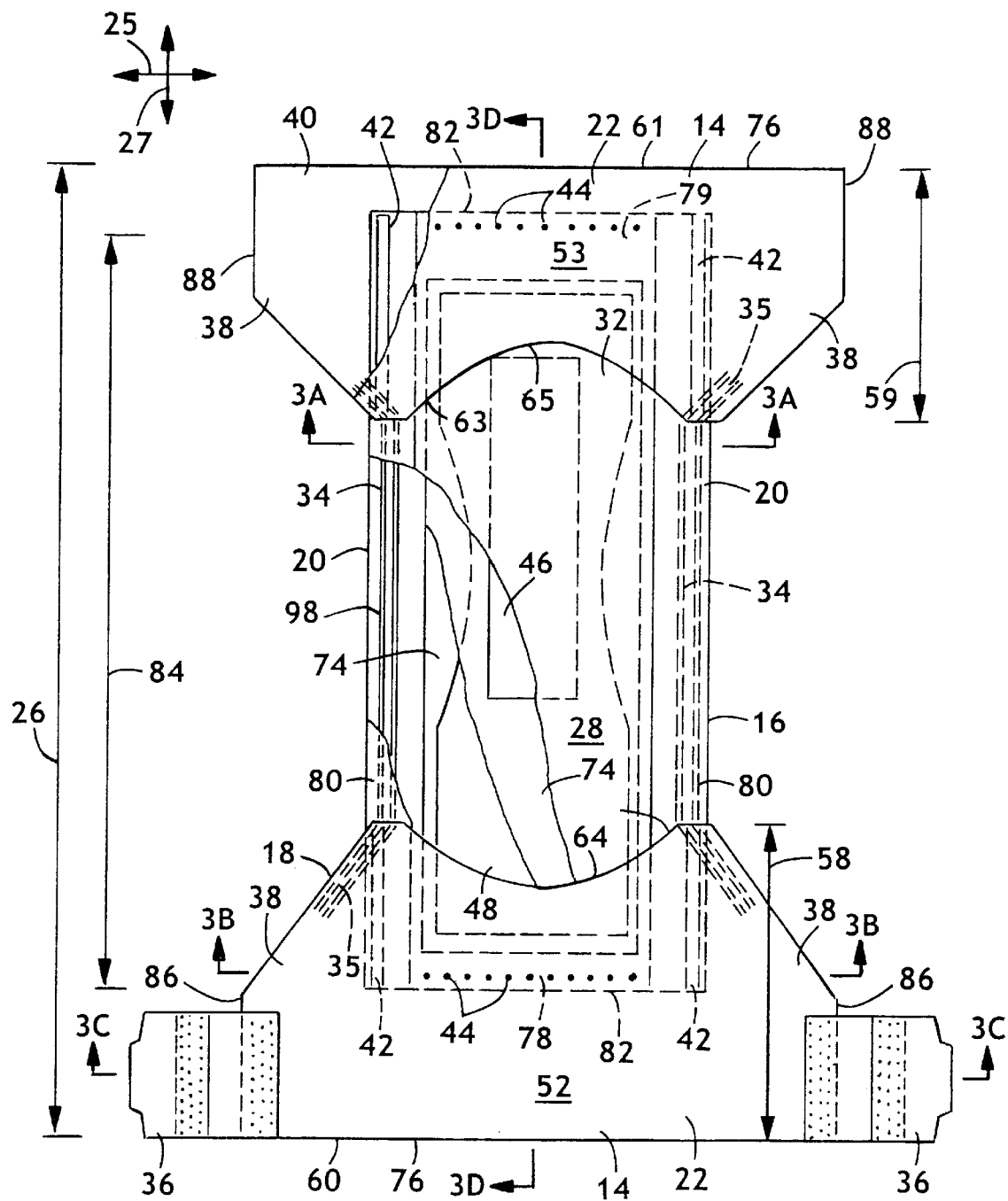
Figure 3A:
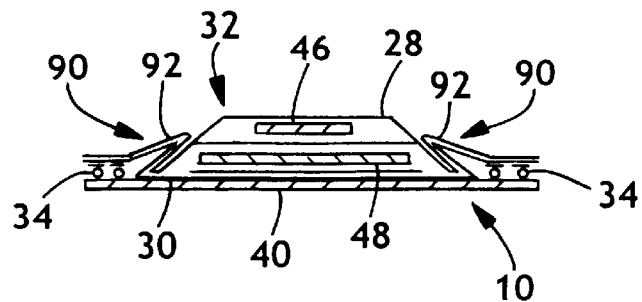

In desired arrangements, at least a medial portion 64 of the laterally extending and longitudinally inboard edge 62 of the first body panel 52 can be substantially unattached to bodyside surface of the absorbent composite 32. Similarly, the second body panel 53 can have a longitudinally inboard terminal end edge 63, and at least a medial portion 65 of the end edge 63 can be substantially unattached to the absorbent composite 32. Either or both of the inboard edges may be substantially straight or curved, as desired. In particular aspects, at least a portion of the inboard edge of either or both of the body panels 52 and 53 can be arranged in a configuration which is concave-inboard, as illustrated in FIG. 3. As representatively shown, the appointed concave curvature can commence at each side margin of the absorbent composite, and can traverse generally laterally across the absorbent composite with a middle portion of the curvature displaced toward the longitudinal end of the article. The curvature can help provide an improved conformance of the body panel with the contours of the wearer's body.

In other aspects of the invention, the first longitudinally terminal end edge 82 of substantially the entire absorbent composite 32 can be spaced relatively inboard from the longitudinally outboard, terminal end edge 60 of the first body panel 52. Accordingly, the body panel can extend longitudinally past and project length-wise beyond its corresponding, generally adjacent, terminal end edge 82 of the absorbent composite. Similarly, the second longitudinally terminal end edge 82 of substantially the entire absorbent composite 32 can be spaced relatively inboard from the longitudinally outboard, terminal end edge 61 of the second body panel 53. Accordingly, the second body panel can extend longitudinally past and project length-wise beyond its corresponding, generally adjacent, terminal end edge 83 of the absorbent composite.

During the conditions of ordinary use, the expandable attachment sections 90 can advantageously allow and provide for a controlled expansion of the volume of the absorbent composite 32, especially after the absorbent composite has started absorbing liquids. In the various configurations of the invention, each expandable attachment section 90 may be a separately provided member which is assembled into the article, or may be integrally formed from appointed portions of other existing components of the article. For example, the expandable attachment section may be formed from appointed portions of the backsheet 30, topsheet 28 or operative combinations thereof. In particular aspects of the invention, the vaflous expandable attachment sections can be substantially free of absorbent materials, such as hydrophilic fiber and superabsorbent polymers.

Figure 2:
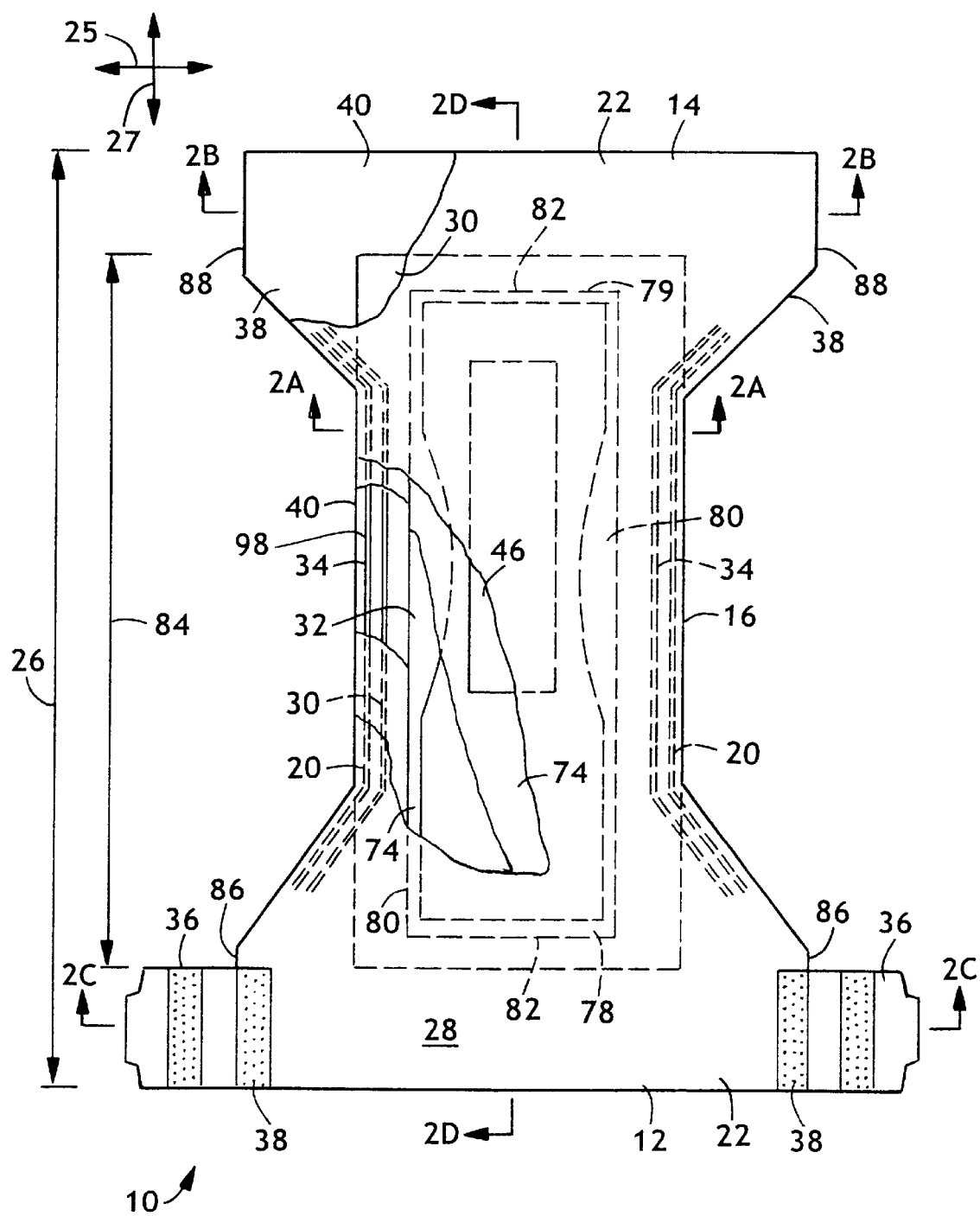
Figure 2A:
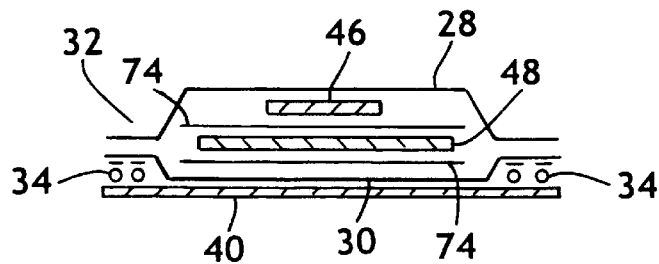
Figure 2B:
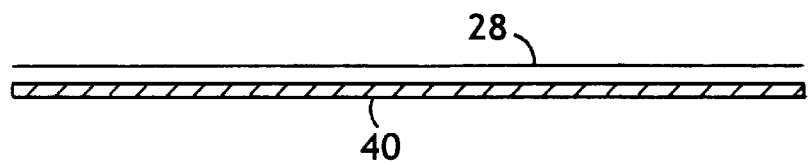
Figure 2C:
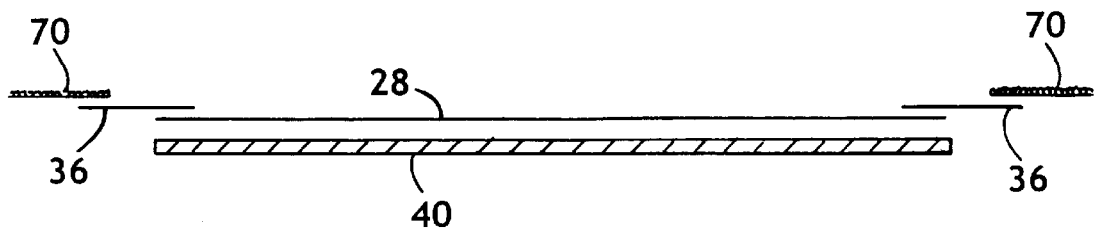
Figure 2D:
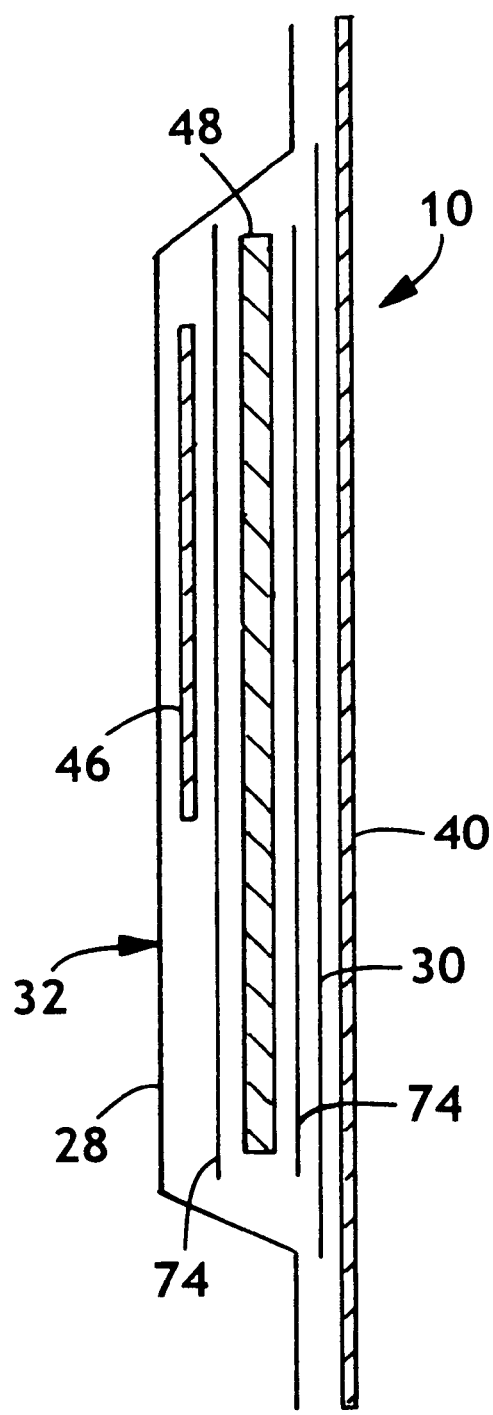
Figure 2E:
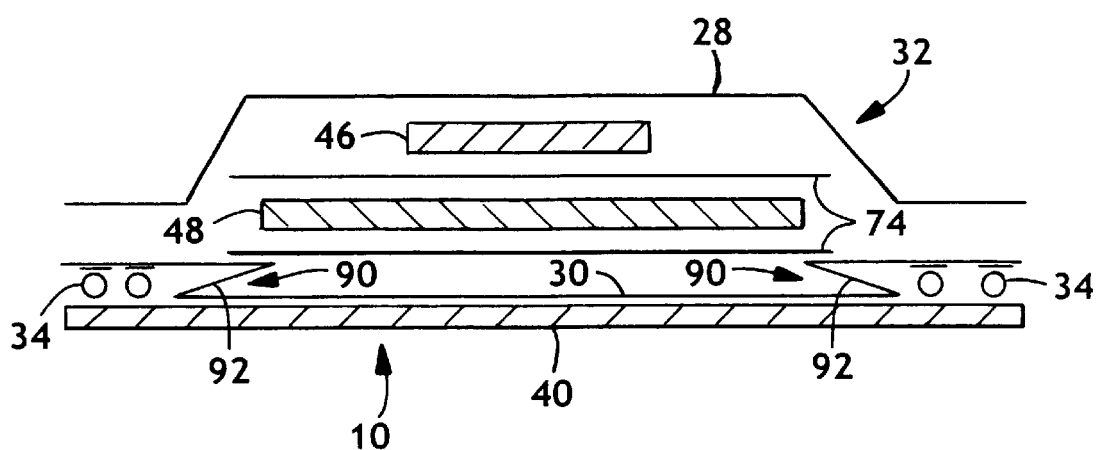

With reference to FIG. 2E, for example, the expandable attachment section 90 can include at least one z-folded pleat portion 92, and the z-folded pleat portion can be provided at each side region 80 of the absorbent composite 32. In the representatively shown arrangements, for example, the pleat portion can provide a predetermined arrangement of interleaved layers which can be flattened together to provide an initial low-volume configuration for the absorbent composite 32. During use and especially during the absorption of liquid, the interleaved layers can operatively move apart to provide a substantially continuous series of one or more, incrementally higher-volume configurations for cooperation with an increasing volume of the absorbent composite, particularly the increasing volume of the retention portion 48.

In particular aspects, the extendible attachment section 90 can include a separately provided component (not shown) which is appointed to interconnect between the absorbent composite 32 and the outward surface 56 of the first body panel 52. The separately provided component may be z-folded.

Alternatively, the substantially z-fold pleat portion 92 can be provided by appointed side marginal sections of the topsheet layer 28 and/or the backsheet layer 30 which extend laterally beyond the terminal side edges of the retention portion 48. As representatively shown in FIGS. 3A and 3B, the z-folded pleat portion may includes side marginal sections of both the topsheet layer 28 and the backsheet layer 30. In this example, the side margins of both the substantially liquid-impermeable backsheet 30 and the substantially liquid permeable topsheet 28 can extend laterally past and project beyond the terminal side edges of the retention portion 48 and wrapsheet 74. The combined side margins of the projecting backsheet and topsheet layers can then be z-folded to form the desired expandable attachment section.

As representatively shown in FIG. 2E, the z-folded pleat portion may alternatively include side marginal sections of only the backsheet layer 30. In this example, the side margins of the substantially liquid-impermeable backsheet 30 can extend laterally past and beyond the terminal side edges of the retention portion 48 and wrapsheet 74. The extended side margins of the backsheet layer 30 can then be z-folded to form the desired expandable attachment section. Optionally, the topsheet layer 28 may also be configured to be laterally extensible.

In the various configurations of the invention, each leg elastic member 34 can be attached to the outward surface of the laterally projecting backsheet layer adjacent to its laterally terminal side edge to extend longitudinally along its associated side margin of the absorbent composite 32. Accordingly, one of the z-folded pleats 92 can be located in each side margin of the absorbent composite and can run along substantially the full length of the absorbent composite.

The relatively outboard edge of each z-folded pleat 92 is operatively attached to its associated body panel 52 or 53 at a location which is positioned inboard from its corresponding, relatively adjacent, longitudinally extending side edge of the associated body panel. Accordingly, the expandable attachment section provided by the pleat 92 can provide a mechanism for allowing the absorbent composite 32 to expand out and away from the body panels and from the wearers body.

With regard to the substantially z-folded pleat members 92, the z-folded pleats extend longitudinally along the article length 26. Desirably, the immediately adjacent panels within the pleat are substantially unattached to each other. Optionally, a small amount of an adhesive or other type of bond may be employed to lightly attach together two or more of the adjacent pleat panels. Such attachment between the pleat panels, however, should be configured with a strength and distribution which do not excessively inhibit the desired expansions of the attachment sections 90. When the retention portion 48 absorbs liquid and increases in volume, the resultant expansion of the retention portion exerts a tensile stress and tensile force on the expandable attachment sections 90. The subsequent expansion of the attachment sections 90 operatively relieves the applied stresses and forces, and increases the volume of the retention portion 48 in a manner which allows the retention portion to grow outwardly away from the first body panel 52. As a result, the first body panel 52 can maintain its desired fit closely about a wearers body, and can better resist the formation of gaps or sags that might allow excessive, undesired leakage.

Figure 6:
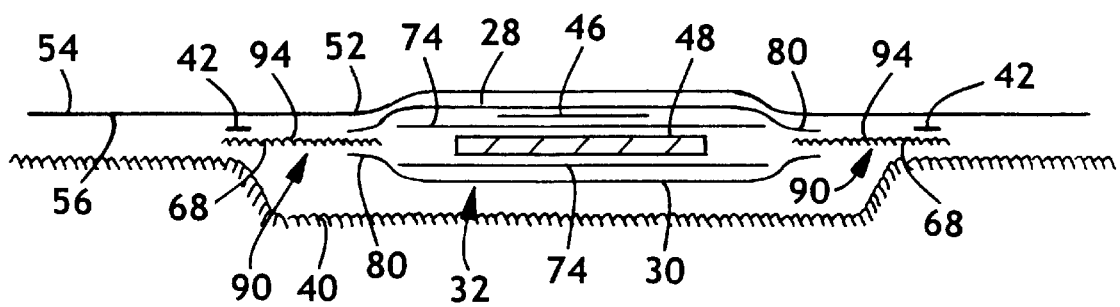

Other aspects of the invention can have expandable attachment sections 90 in which a laterally extensible region 68 (e.g. FIG. 6) is configured to interconnect between the absorbent composite 32 and the outward surface 56 of the appointed body panel 52 or 53, as appropriate. The extensible region 68 may be formed from various suitable materials, such woven or nonwoven creped fabrics, creped films, apertured films, knitted fabrics and the like, as well as combinations thereof. In this configuration, each leg elastic members 34 can be attached to an inward or outward surface of its corresponding extensible region 68 adjacent to an outboard, laterally terminal, side edge of the extensible member to extend longitudinally of the article.

Figure 7:
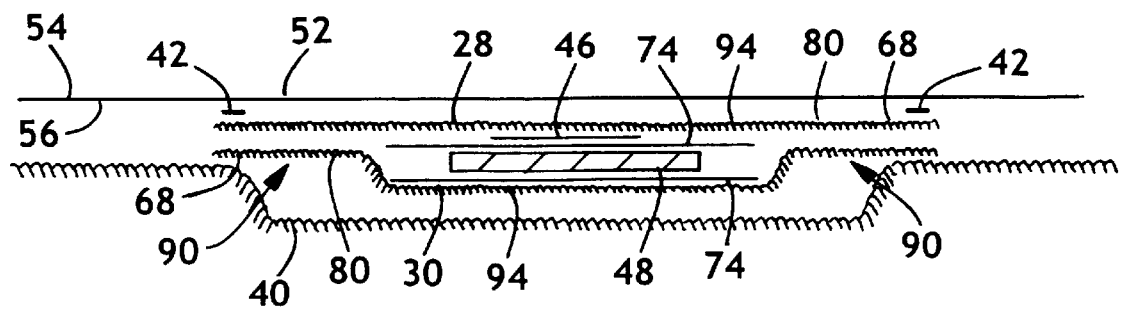
Figure 7A:
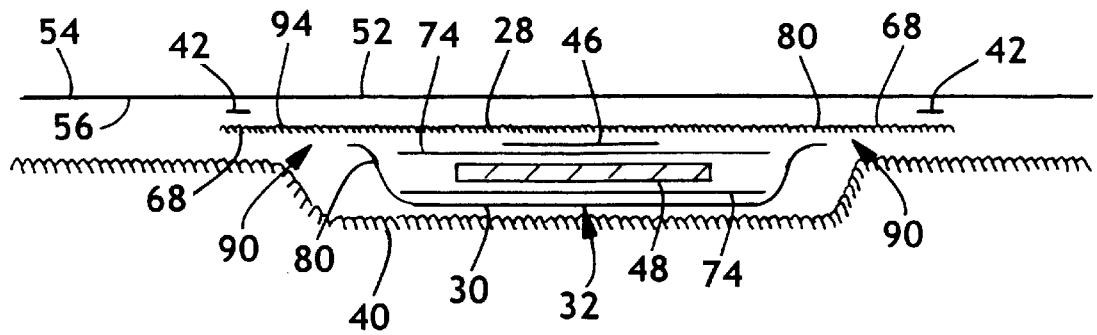
Figure 7B:
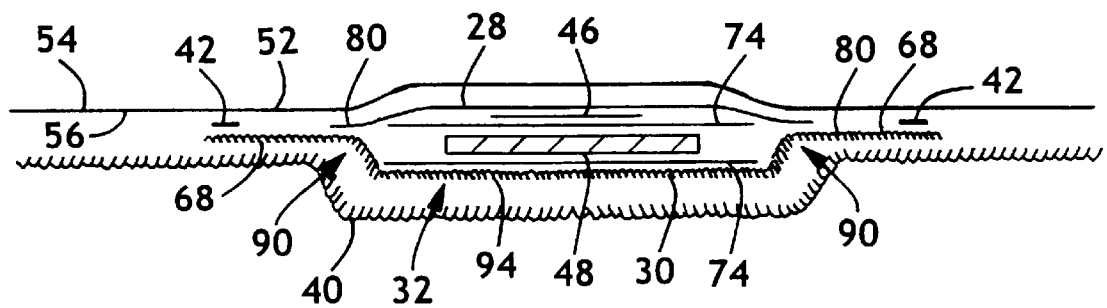

In particular aspects, the extensible region 68 may include a separately provided 20 component or member which is assembled and attached into the article (e.g. FIG. 6) Accordingly, the leg elastic members 34 may not be directly attached to the absorbent composite 32. Alternatively, the extensible member 68 may be integrally formed with or from another existing component, such as the topsheet layer 28 (e.g. Figs. 5A, 5B, 7 and 7A) or the backsheet 30 (FIGS. 7 and 7B). At least a portion of the extensible topsheet or backsheet may extend lateral past and project beyond the terminal side edges of the retention portion 48 and wrapsheet layers 74.

With reference to FIGS. 5A, 5B, 7, 7A and 7B, for example, the extensible member can have a plurality of micropleats 94 formed therein. As representatively shown, the micropleated component 94 can be a separately provided and assembled into the article at a location which is interposed between the absorbent composite 32 and the outward surface 56 of the first body panel 52. Alternatively, the micropleated component 94 can be integrally provided by substantially unitary sections of the topsheet layer 28 and/or backsheet layer 30. The unitary sections can extend laterally beyond the terminal side edges of the retention portion 48, and have the desired micropleats formed therein. The micropleated materials may include woven fabrics, nonwoven fabrics, polymer films and the like, as well as combinations thereof which have been processed to generate the desired micropleats. Such processing can, for example, include conventional creping and microcreping techniques.

In further aspects, the expandable attachment sections 90 can include an elastomeric material which is elastomerically stretchable at least along the article width 24. The elastomeric material can be composed of films, strands, laminated composites or the like, as well as combinations thereof. For the purposes of the present description, an elastomeric material is capable of being stretched to a 67% elongation and then retracting. After retracting, the retraction force at 50% elongation is at least a minimum of about 40 grams-force (gmf) per inch of cross-wise length of the material (about 16 gmf per cm of cross-wise length; about 0.15 Newtons per cm of cross-wise length). Additionally, the retraction force at 20% elongation is at least 10 gmf per inch of cross-wise length (about 4 gmf per cm of cross-wise length; about 0.04 Newtons per cm of cross-wise length). The cross-wise length is measured perpendicular to the direction of the applied stretching force. For a test sample taken from the illustrated configurations, the cross-wise length of the sample would lie generally along the article longitudinal direction 27.

In still other configurations, the backsheet layer 30 may include an elastomeric material which is elastomerically stretchable along the article width 24, as representatively shown in FIGS. 7 and 7B. Each laterally opposed side region 80 of the absorbent composite 32 can include a corresponding, laterally opposed side region of the backsheet layer 30. Each side region of the backsheet layer desirable extends laterally beyond their corresponding terminal side edges of the retention portion 48.

In particular aspects of the invention, each expandable attachment section 90 can provide a transverse elongation (along the lateral direction 25) of at least about 1 cm when subjected to an applied, lateral tensile force of 30 grams-force (gmf) per inch of cross-wise length of the expandable attachment section (about 12 gmf per cm of cross-wise length; about 0.12 Newtons per cm of cross-wise length). Alternatively, the expandable attachment section 90 can provide an elongation of at least about 2 cm, and optionally, an elongation of at least about 4 cm under the applied tensile force to afford improved performance. In other aspects, the expandable attachment section 90 can provide an elongation of not more than about 12 cm under an applied tensile force of 50 gmf per inch of cross-wise length of the expandable attachment section (about 20 gmf per cm of cross-wise length; about 0.19 Newtons per cm of cross-wise length). Alternatively, the expandable attachment section can provide an elongation of not more than about 10 cm, and optionally is not more than about 8 cm to afford improved benefits. For the purposes of this elongation parameter, the cross-wise length of the expandable attachment section is measured perpendicular to the applied tensile force. For a sample taken from the illustrated configurations of the invention, the cross-wise length of the sample would lie generally along the article longitudinal direction 27.

A suitable technique for generating a representative tensile-load vs. extension curve, and for determining the amount of elongation and/or retractive force parameters of a selected component or material can employ ASTM Standard Test Method D882 (Tensile Method for Tensile Properties of Thin Plastic Sheeting) dated December 1995, with the following particulars. The "width" of the test sample will be a cross-wise width which can be conveniently obtained from the product being tested, and is desirably about 2 inch (about 5.04 cm). The test sample width is perpendicular to the direction of the tensile force applied during the testing. With regard to the shown configurations, for example, the test sample "width" generally corresponds to the length-wise dimension of the expandable attachment section 90 or other component (e.g. outercover layer 40) along the longitudinal direction 27 of the article. The initial separation of the jaws of the tensile tester is 3 inches (7.62 cm), and the moving jaw is moved at a constant rate of 50 mm/min. The moving jaw is stopped at an extension of 50 mm for a period of 10 sec, and then returned back to its initial starting position at a rate of 50 mm/min. The force-extention curve to the complete tension and retraction cycle can be recorded on a conventional computer equipped with commercially available software, such as TestWorks for Windows, version 3.09, which is available from MTS System Corporation, a business having a location at 14000 Technology Drive, Eden Prairie, MN. The obtained data is normalized and reported in appropriate units of force per unit length of sample "width" ( e.g. grams-force per inch, or Newtons per inch, or grams-force per centimeter, or Newtons per centimeter).

Figure 3B:
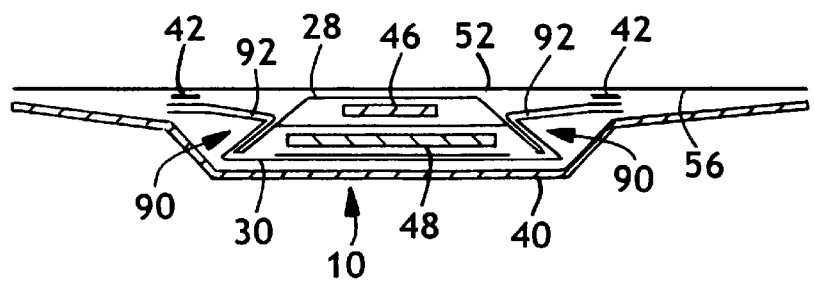
Figure 3C:
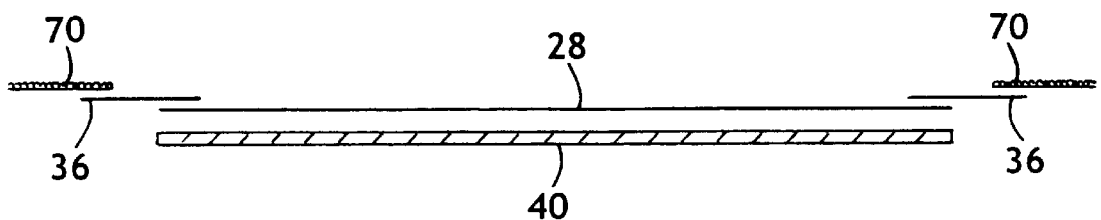
Figure 3D:
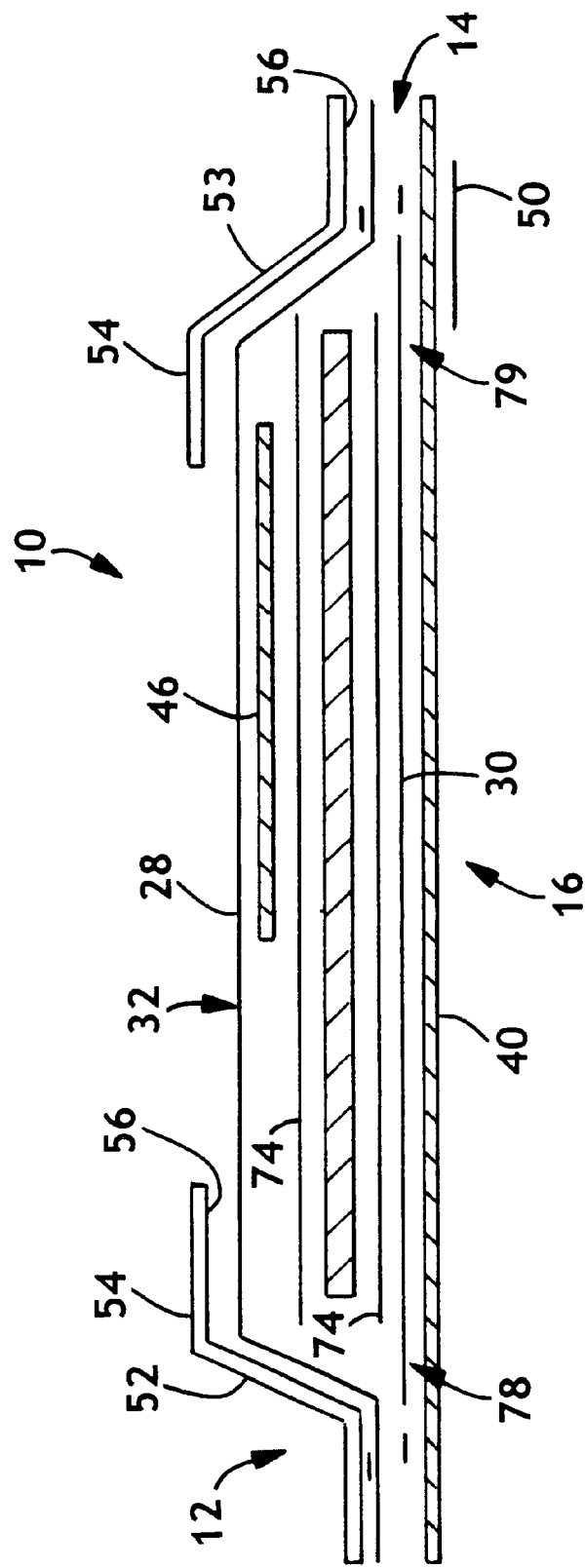

With reference to FIGS. 3 and 3B, each appointed expandable attachment section 90 can be bonded or otherwise affixed to its correspondingly associated region of the body panel with an operative side securement 42. Each side securement 42 may be substantially continuous or discontinuous, and may be distributed randomly or in a selected area pattern. In addition, the article of the invention can include a first, laterally extending, end attachment 44 which is distributed along at least a portion of the first end region 78 of the absorbent composite 32 to help secure the end of the absorbent composite to the body panel 52. The end attachment 44 may also be configured to provide a sealing, liquid-barrier attachment which can help resist a passage of liquid between the absorbent composite and the outward surface 56 of the first body panel 52. Similarly, a second laterally extending end attachment 44 can be distributed along at least a portion of the second end region 79 of the absorbent composite 32 to secure the second end of the absorbent composite to the second body panel, and to help resist a passage of liquid between the absorbent composite and the outward surface 56 of the second body panel 53.

The side securements 42 and end attachments 44 can be provided by various suitable mechanisms. For example, each of the side securements 42 and end attachments 44 may include adhesive bonds, thermal bonds, ultrasonic bonds, pins, staples, or the like, as well as combinations thereof.

In the representatively shown configuration, each end attachment 44 is provided by a plurality of individually spaced apart, thermal or ultrasonic bonds arranged in a selected pattern. The pattern bond may be regular or irregular in distribution, and is operatively configured to provide the desired securement, expandability and/or leakage resistance in the article. Each end attachment 44 may alternatively include a laterally extending bond which is substantially continuous along a major portion of the lateral width of the absorbent composite. Similarly, each side securement 42 may include a longitudinally extending bond which is substantially continuous along a major portion of the longitudinal length of the article portion at which each expandable attachment section is operably affixed to its corresponding, associated body panel.

In particular aspects of the invention, either or both of the body panels 52 and 53 may be composed of a wide range of materials with various basis weights and properties. For example, the body panel material may include knitted or other woven fabrics, nonwoven fabrics, polymer films, laminates, and the like, as well as combinations thereof. It should be readily appreciated that each of the individual body panels may be composed of different materials, or of substantially the same material.

In the various configurations of the invention, the basis weight of the body panel material can be at least a minimum of about 10 g/m². Alternatively, the basis weight can be at least about 20 g/m², and optionally, can be at least about 40 g/m² to provide improved benefits. In further aspects, the basis weight of the body panel material can be not more than a maximum of about 100 g/m². Alternatively, the basis weight can be not more than about 80 g/m², and optionally, can be not more than about 60 g/m² to provide improved performance.

In the differing configurations of the invention, the body panel material may be substantially permeable to air or substantially impermeable to air. The body panel material also may be substantially liquid-permeable or substantially liquid-impermeable. In particular arrangements, the body panel material may be substantially nonelastomeric. In other aspects, the body panels 52 and/or 53 can include an elastomeric material which is elastomerically stretchable at least along the lateral article width 24. Examples of such elastomeric materials can include a neck-bonded-laminate (NBL), a stretch-bonded-laminate (SBL), a necked-thermal laminate, or the like, as well as combinations thereof. Such laminates can provide an improved combination of cloth-like feel and elastomeric stretchability.

In desired configurations, the elastomeric body panel material can provide an elastomeric, stretch elongation which is at least about 3%, and desirably is at least about 5%. Alternatively, the stretch elongation can be at least about 10%, and optionally, can be at least about 20% to provide improved performance. In other aspects, the elastomeric stretch elongation can be not more than about 200% and desirably can be not more than about 100%. Alternatively, the stretch elongation can be not more than about 50%, and optionally, can be not more than about 30% to provide improved performance.

The percentage of elastomeric stretch or other elongation can be determined in accordance with the following formula: $100*(L-L_o)/(L_o)$;
where:
L=stretched length,
$L_o$=initial length,
In addition, the amount of stretch elongation is determined under an applied tension force of 250 gram-force per inch of width measured perpendicular to the direction of the applied tension.

With reference to FIG. 3, the first body panel 52 and/or the second body panel 53 can have a longitudinal length 58, 59 which is not more than a maximum of about 80% of the article length 26. Alternatively, either or both body panels can alternatively have a longitudinal length which is not more than about 65% of the article length 26, and optionally, is not more than about 50% of the article length to provide improved benefits. In desired arrangements, the longitudinal length of the body panel can be not more than about 40%. In further arrangements, the longitudinal length of the body panel can be not more than about 35%, and optionally not more than about 30% of the article length to provide improved performance.

In other aspects of the invention, the first body panel 52 and/or the second body panel 53 can have a longitudinal length which is at least a minimum of about 5% of the article length 26. Alternatively, at least one of the body panels (or both) can have a longitudinal length which is at least about 10% of the article length, and optionally, is at least about 15% of the article length to provide improved performance. Desirably, at least one of the go body panels, particularly the back body panel, can have a longitudinal length which is at least about 2 cm. More desirably the selected body panel can have a longitudinal length which is at least about 4 cm, and optionally, is at least about 6 cm to provide improved fit and skin dryness.

With reference to FIGS. 1, 2 and 3, each of the leg elastic members 34 can include a plurality of elastomeric strands 98. Optionally, each leg elastic member may be a composite which includes at least one carrier layer (not shown), and the elastomeric strands can be operatively attached to the carrier layer. Various mechanisms, such as adhesive, thermal bonds, sonic bonds, or the like as well as combinations thereof, can be employed to provide the desired attachments between the elastomeric strands 98 and the leg carrier layer. In the representatively shown arrangement, each leg elastic member is a laminate composed of a plurality of elastomeric strands sandwiched and held between a pair of carrier layers.

The carrier layer is desirably composed of a woven or nonwoven fabric having a basis weight within the range of about 10–50 g/m$^2$, but may optionally be composed of a polymer film material. For example, the shown carrier layers may be composed of a polypropylene spunbond nonwoven fabric, and the pair of carrier layers may be adhesively bonded together with a suitable pattern of adhesive, such as a swirl-pattern of pressure-sensitive adhesive.

As representatively shown, each of the leg elastic members 34 can be operatively attached to an outward surface of at least a portion of the lateral side edge margins 20 of the article. In the shown configuration, for example, the side edge margins 20 of the article are provided by side edge portions of the absorbent composite 32 which extend laterally beyond the laterally opposed, terminal side edges of the retention portion 48. It should be readily appreciated that any of the conventional attaching mechanisms described in the present disclosure may be employed to secure the leg elastic members into the article. In the representatively shown arrangement, the attachment mechanism includes a distributed pattern of sonic bonds. In other aspects of the invention, each of the leg elastic members 34 may be operatives attached to an inward, bodyside surface of its corresponding side edge margin 20 of the article.

Each of the leg elastic members 34 can include at least one longitudinal end section 35 which diverges away from the absorbent composite 32. In the representatively shown embodiments, each leg elastic member 34 as a pair of longitudinally opposed end sections, each of which diverges away from the absorbent composite 32. The end sections of the leg elastic members 34 can be attached to the outward surface 56 of its corresponding body panel 52, 53.

The elastic members 34 may have any of a multitude of configurations. For example, the width of the individual elastic members 34 may be varied from about 0.25 millimeters (0.01 inch) to about 25 millimeters (1.0 inch) or more. The elastic members may comprise a single strand of elastic material, or may comprise several parallel or non-parallel strands of elastic material, or may be applied in a rectilinear or curvilinear arrangement. Where the strands are non-parallel, two or more of the strands may intersect or otherwise interconnect within the elastic member. The elastic members may be affixed to the diaper in any of several ways which are known in the art. For example, the elastic members may be ultrasonically bonded, heat and pressure sealed using a variety of bonding patterns, or adhesively bonded to diaper 10 with sprayed or swirled patterns of hotmelt adhesive.

In particular embodiments of the invention, the leg elastic members 34 may include a carrier sheet to which are attached a grouped set of elastics composed of a plurality of individual elastic strands. The elastic strands may intersect or be interconnected, or be entirely separated from each other. The carrier sheet may, for example, comprise a 0.002 cm thick polymer film, such as a film of unembossed polypropylene material. The elastic strands can, for example, be composed of LYCRA elastomer available from DuPont, a business having offices in Wilmington, Del. Each elastic strand is typically within the range of about 470–1500 decitex (dtx), and may be about 940–1050 dtx. In particular embodiments of the invention, for example, three or four strands can be employed for each elasticized legband.

In addition, the leg elastics 34 may be generally straight or optionally curved. For example, the curved elastics can be inwardly bowed toward the longitudinal centerline of the diaper. In particular arrangements, the curvature of the elastics may not be configured or positioned symmetrically relative to the lateral centerline of the diaper. The curved elastics may have an inwardly bowed and outwardly bowed, reflex-type of curvature, and the length-wise center of the elastics may optionally be offset by a selected distance toward either the front or rear waistband of the diaper to provide desired fit and appearance. In particular embodiments of the invention, the innermost point (apex) of the set of curved elastics can be offset towards the front or rear waistband of the diaper, and the outwardly bowed reflexed-portion can be positioned toward the diaper front waistband.

The diaper 10 can include a waist elastic positioned in the longitudinal margins of either or both of the front waistband 14 and the rear waistband 12. The waist elastics may be composed of any suitable elastomeric material, such as an elastomer film, an elastic foam, multiple elastic strands, an elastomeric fabric or the like. For example, suitable elastic waist constructions are described in U.S. Pat. No. 4,916,005 to Lippert et al., the entire disclosure of which is hereby incorporated by reference in a manner that is consistent herewith.

With reference to the representative configurations shown in FIGS. 1 and 2, the article can include "ear" regions 38. In particular arrangements, each ear region 38 extends laterally at the opposed, lateral ends of at least one waistband portion of backsheet 30, such as the representatively shown rear waistband portion 12, to provide terminal side sections of the article. In addition, each ear region can substantially span from a laterally extending, terminal waistband edge 76 to approximately the location of its associated and corresponding leg opening section of the diaper. The diaper 10, for example, has a laterally opposed pair of leg openings provided by the curved margins of the ear regions in combination with the correspondingly adjacent, medial sections of the shown pair of longitudinally extending, side edge regions 20 (e.g. FIG. 1). In alternative configurations, the ear regions may be provided by a system of separately provided ear members (not shown).

In the various configurations of the invention, the ear regions may be integrally formed with a selected diaper component. For example, ear regions 38 can be integrally formed from the layer of material which provides backsheet layer 30, or may be integrally formed from the material employed to provide topsheet 28. In alternative configurations, the ear regions 38 may be provided by one or more separately provided members that are connected and assembled to the backsheet 30, to the topsheet 28, in between the backsheet and topsheet, or in various fixedly attached combinations of such assemblies.

In particular configurations of the invention, each of the ear regions 38 may be formed from a separately provided piece of material which is then suitably assembled and attached to the selected front and/or rear waistband portion of the diaper article. For example, each ear region 38 may be attached to the rear waistband portion of the backsheet 30 along an ear region attachment zone, and can be operably attached to either or both of the backsheet and topsheet components of the article. The inboard, attachment zone region of each ear region can be overlapped and laminated with its corresponding, lateral end edge region of the waistband section of the article. The ear regions extend laterally to form a pair of opposed waist-flap sections of the diaper, and are attached with suitable connecting means, such as adhesive bonding, thermal bonding, ultrasonic bonding, clips, staples, sewing or the like, Desirably, the ear regions extend laterally beyond the terminal side edges of the backsheet layer and topsheet layer at the corresponding, attached waistband section of the article.

The ear regions 38 may be composed of a substantially non-elastomeric material, such as polymer films, woven fabrics, nonwoven fabrics or the like, as well as combinations thereof. In particular aspects of the invention, ear regions 38 may be composed of a substantially elastomeric material, such as a stretch-bonded-laminate (SBL) material, a neck-bonded-laminate (NBL) material, an elastomeric film, an elastomeric foam material, or the like, which is elastomerically stretchable at least along the lateral direction 25. For example, suitable meltblown elastomeric fibrous webs for forming ear regions 38 are described in U.S. Pat. No. 4,663,220 issued May 5, 1987 to T. Wisneski et al., the entire disclosure of which is hereby incorporated by reference. Examples of composite fabrics comprising at least one layer of nonwoven textile fabric secured to a fibrous elastic layer are described in European Patent Application EP 0 217 032 A2 published on Apr. 8, 1987 which has the listed inventors of J. Taylor et al., the entire disclosure of which is hereby incorporated by reference. Examples of NBL materials are described in U.S. Pat. No. 5,226,992 issued Jul. 13, 1993 to Mormon, the entire disclosure of which is hereby incorporated by reference.

As previously mentioned, various suitable constructions can be employed to attach the ear regions 38 to the selected waistband portions of the article. Particular examples of suitable constructions for securing a pair of elastically stretchable members to the lateral, side portions of an article to extend laterally outward beyond the laterally opposed side regions of the outercover and liner components of an article can be found in U.S. Pat. No. 4,938,753 issued Jul. 3, 1990 to P. VanGompel et al., the entire disclosure of which is hereby incorporated by reference in a manner that is consistent herewith.

Each of the ear regions 38 extends laterally at a one of the opposed lateral ends of at least one waistband section of the diaper 10. In the shown embodiment, for example, a first pair of ear regions extend laterally at the opposed lateral ends of the back waistband section of the backsheet 30, and a second pair of ear regions extend laterally at the opposed lateral ends of the front waistband section of the backsheet. The ear regions can have a tapered, curved or otherwise contoured shape in which the length of the base region is smaller or larger than the length of its relatively outboard end region. The ear regions may, for example, have a substantially rectangular shape or a substantially trapezoidal shape.

Diaper 10 can also include a pair of elasticized containment flaps (not shown) which can extend generally lengthwise along the longitudinal direction 27 of the diaper. The containment flaps are typically positioned laterally inboard from leg elastics 34, and substantially symmetrically placed on each side of the lengthwise, longitudinal centerline of the diaper. In the illustrated arrangements, each containment flap has a substantially fixed edge portion and a substantially moveable edge portion, and is operably elasticized with at least one elastomeric member to help each containment flap to closely contact and conform to the contours of the wearer's body. Examples of suitable containment flap constructions are described in U.S. Pat. No. 4,704,116 issued Nov. 3, 1987, to K. Enloe, the entire disclosure of which is hereby incorporated by reference in a manner that is consistent herewith. The containment flaps may be composed of a wettable or a non-wettable material, as desired. In addition, the containment flap material may be substantially liquid-impermeable, may be permeable to only gas or may be permeable to both gas and liquid. Other suitable containment flap configurations are described in U.S. patent application Ser. No. 206,816 of R. Everett et al., filed Mar. 4, 1994 and entitled ABSORBENT ARTICLE HAVING AN IMPROVED SURGE MANAGEMENT which corresponds to U.S. Pat. No. 5,562,650, the disclosure of which is hereby incorporated by reference in a manner that is consistent herewith.

Figure 1B:
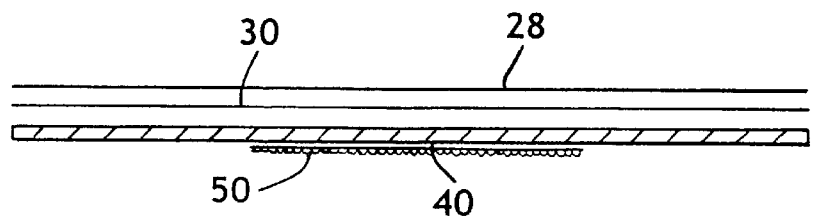
Figure 1C:
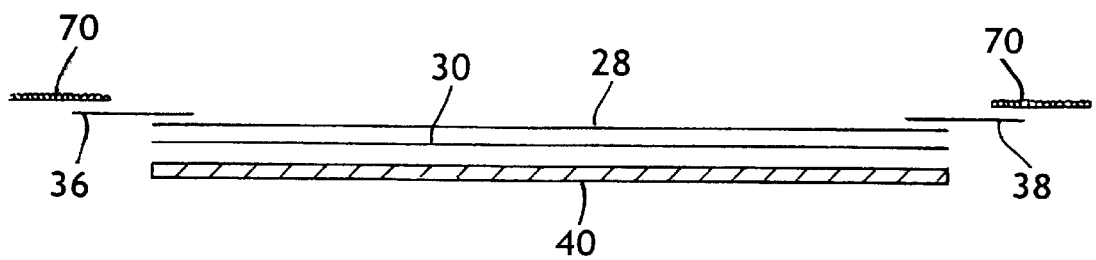
Figure 1D:
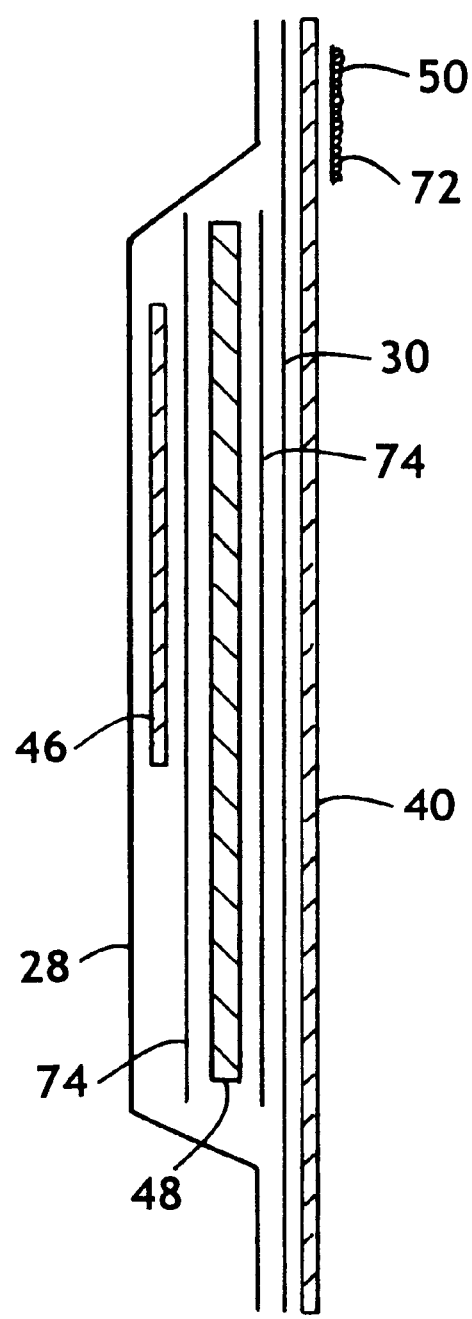
Figure 1E:
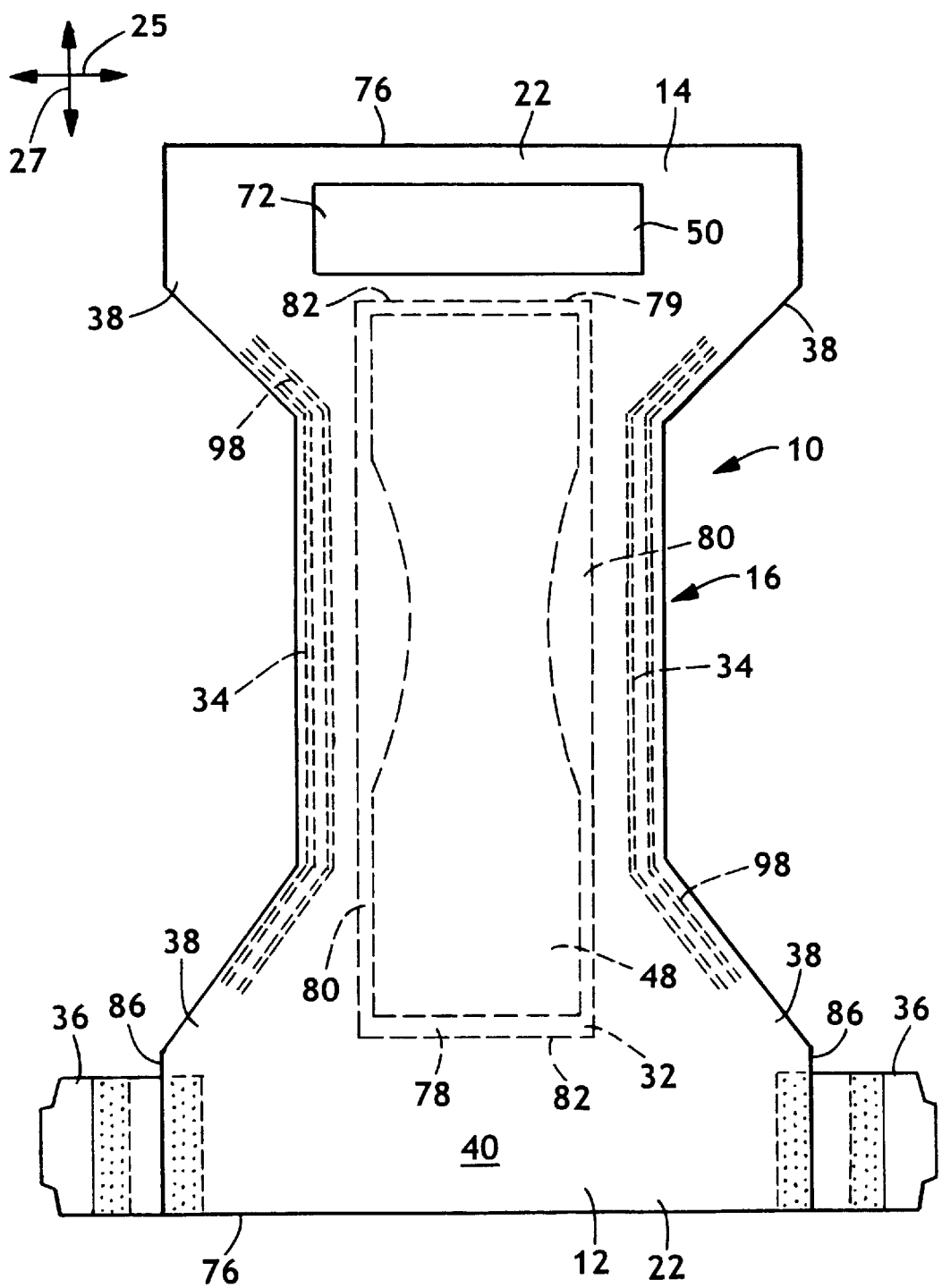

To provide a desired refastenable fastening system, diaper 10 can include one or more appointed landing member regions, such as a first, primary landing member 50 (e.g. FIGS. 1B and 1E), which can provide an operable target area for receiving a releasable and re-attachable securement of the fastener tabs 36 thereon. In particular embodiments of the invention, the landing member patch can be positioned on the front waistband portion 14 of the diaper, and can be located at an operative section of an outer surface of the article, such as the outward surface of the outercover 40. The fastening mechanism between the landing member and the fastener tabs 36 may be adhesive, cohesive, mechanical or combinations thereof. In the context of the present invention, a mechanical fastening system is a system which includes cooperating components which mechanically inter-engage to provide a desired securement.

A configuration which employs a releasable, interengaging mechanical fastening system can, for example, locate a first element or component of the mechanical fastener on the fastener tab 36 and a second, cooperating element or component of the mechanical fastener on the landing zone member 50. For example, with a hook-and-loop fastener, the hook material can be operably connected and affixed to the fastener tabs 36 and the loop material can be operably connected and affixed to the landing member 50. Alternatively, the loop material can be operably connected to the fastener tabs 36 and the hook material can be operably connected to the landing member 50.

In the various embodiments of the invention, a separately provided tape fastener tab 36 can be located at either or both of lateral end regions 86 and 88 of either or both of the waistbands 14 and 12. The representatively shown embodiment, for example, has one of the fastener tabs 36 located at each of the distal side edges of the rear waistband 12. More particularly, each of the fasteners 36 is assembled and attached to extend from a corresponding, immediately adjacent ear region at one of the opposed lateral ends of the back waistband section 12.

In the various configurations of the invention, the first and/or second fastening component may include an adhesive, a cohesive, a complementary element of an interengaging mechanical fastening system, or the like, as well as combinations thereof. The mechanical fastener components can be provided by mechanical-type fasteners such as hooks, buckles, snaps, buttons and the like, which include cooperating and complementary, mechanically interlocking components. For example, the mechanical fastening system is may be a hook-and-loop type of fastening system. Such fastening systems generally comprise a "hook" or hook-like, male component, and a cooperating "loop" or loop-like, female component which engages and releasably interconnects with the hook component. Desirably, the interconnection is selectively releasable and re-attachable. Conventional systems are, for example, available under the VELCRO trademark. The hook element may be provided by a single or multiple hook configuration, such as provided by a mushroom-head type of hook element. The loop element may be provided by a woven fabric, a nonwoven fabric, a knitted fabric, a perforated or apertured layer, and the like, as well as combinations thereof. The many arrangements and variations of such fastener systems have been collectively referred to as hook-and-loop fasteners.

In desired arrangements of the invention, the first fastening component fastening component may include a hook type of mechanical fastening element. Accordingly, the corresponding landing member component can include a complementary loop element. It should also be readily apparent that, in the various configurations of the invention, the relative positions and/or materials of the fastening component and its corresponding landing member component can be transposed. For example, in a hook-and-loop fastening system, the first fastening component may optionally be composed of the loop element and the landing member component may be provided by the hook-type element. element of suitable hook-and-loop fastening systems are described in U.S. Pat. No. 5,019,073 issued May 28, 1991 to T. Roessler et al., the entire disclosure of which is hereby incorporated by reference in a manner that is consistent herewith. Other examples of hook-and-loop fastening systems are described in U.S. patent application Ser. No. 366,080 entitled HIGH-PEEL TAB FASTENER, filed Dec. 28, 1994 by G. Zehner et al. (attorney docket No. 11,571) which corresponds to U.S. Pat. No. 5,605,735; and U.S. patent application Ser. No. 421,640 entitled MULTI-ATTACHMENT FASTENING SYSTEM, filed Apr. 13,1995 by P. VanGompel et al.; the entire disclosures of which are hereby incorporated by reference in a manner that is consistent herewith. Examples of fastening tabs constructed with a carrier layer are described in U.S. patent application Ser. No. 08/603,477 of A. Long et al., entitled MECHANICAL FASTENING SYSTEM WITH GRIP TAB and filed Mar. 6, 1996 which corresponds to U.S. Pat. No. 5,624,429, the entire disclosure of which is hereby incorporated by reference in a manner which is consistent herewith.

In a typical configuration of a hook-and-loop fastening system, the hook material member is operably connected to the fastening tab 36, and the loop material is employed to construct at least one cooperating landing member 50. The landing member can, for example, be suitably positioned on the exposed, outward-side surface of the extensible outercover 40. As previously mentioned, an alternative configuration of the hook-and-loop fastening system may have the loop material secured to the fastener tab 36 and may have the hook material employed to form the landing member 50.

In the various aspects and configurations of the invention, the hook element material can be of the type referred to as micro-hook material. A suitable micro-hook material is distributed under the designation CS200 and is available from 3M Company, a business having offices in St. Paul, Minn.. The micro-hook material can have hooks in the shape of mushroom "caps", and can be configured with a hook density of about 1600 hooks per square inch; a hook height which is within the range of about 0.033–0.097 cm (about 0.013 to 0.038 inch); and a cap width which is within the range of about 0.025–0.033 cm (about 0.01 to 0.013 inch). The hooks are attached to a base film substrate having a thickness of about 0.0076–0.01 cm (about 0.003–0.004 inch) and a Gurley stiffness of about 15 mgf.

Another suitable micro-hook material is distributed under the designation VELCRO CFM-29 1058, and is available from VELCRO U.S.A., Inc., a business having offices in Manchester, N.H.. The micro-hook material can have hooks in the shape of angled hook elements, and can be configured with a hook density of about 264 hooks per square centimeter (about 1700 hooks per square inch); a hook height which is within the range of about 0.030–0.063 cm (about 0.012–0.025 inch); and a hook width which is within the range of about 0.007 to 0.022 cm (about 0.003 to 0.009 inch). The hook elements are coextruded with a base layer substrate having a thickness of about 0.0076–0.008 cm (about 0.003–0.0035 inch), and the member of hook material has a Gurley stiffness of about 12 mgf (about 12 Gurley units).

For the purposes of the present invention, the various stiffness values are determined with respect to a bending moment produced by a force which is directed perpendicular to the plane substantially defined by the length and width of the component being tested. A suitable technique for determining the stiffness values described herein is a Gurley Stiffness test, a description of which is set forth in TAPPI Standard Test T 543 om-94 (Bending Resistance of Paper (Gurley type tester)). A suitable testing apparatus is a Gurley Digital Stiffness Tester; Model 4171-D manufactured by Teledyne Gurley, a business having offices in Troy, N.Y. For purposes of the present description, the stated Gurley stiffness values are intended to correspond to the values that would be generated by a "standard" sized sample. Accordingly, the scale readings from the Gurley stiffness tester are appropriately converted to the stiffness of a standard size sample, and are traditionally reported in terms of milligrams of force (mgf). Currently, a standard "Gurley unit" is equal to a stiffness value of 1 mgf, and may equivalently be employed to report the Gurley stiffness.

In the various aspects and configurations of the invention, the loop material can be provided by a nonwoven, woven or knit fabric. For example, a suitable loop material fabric can be composed of a 2 bar, warp knit fabric of the type available from Guilford Mills, Inc., Greensboro, N.C. under the trade designation #4285, as well other of knit fabrics. Suitable loop materials are also available from the 3M Company, which has distributed a nylon woven loop under their SCOTCHMATE brand. The 3M Company has also distributed a liner-less loop web with adhesive on the backside of the web, and 3M knitted loop tape.

In particular aspects of the invention, the loop material need not be limited to a discrete landing member patch. Instead the loop material can, for example, be provided by a substantially continuous, outer fibrous layer which is integrated to extend over substantially the total exposed surface area of a cloth-like, extensible outercover 40 employed with the article. The resultant, extensible outercover 40 can thereby provide the loop material for an operative "fasten anywhere" mechanical fastening system.

In the various configurations of the invention, the engagement force between the particular fastening component and its appointed landing member component should be large enough and durable enough to provide an adequate securement of the article on the wearer during use. In desired configurations, the engagement force can provide a peel force value of not less than about 75 grams-force (gmf). Alternatively, the peel force is not less than about 100 gmf, and optionally is not less than about 400 gmf. In particular aspects, the peel force is not more than about 1,200 gmf. Alternatively, the peel force is not more than about 800 gmf, and optionally is not more than about 600 gmf. The engagement force can additionally provide a shear force value of not less than about 1,000 gmf. Alternatively, the shear force is not less than about 2,000 gmf, and optionally, is not less than about 3,000 gmf . In further aspects, the shear force is not more than about 10,000 gmf. Alternatively, the shear force is not more than about 9,000 gmf, and optionally is not more than about 8,000 gmf.

The peel force can be determined in accordance with standard procedure ASTM D5170, approved Sep. 15, 1991 and published November 1991. The shear force value can be determined in accordance with the standard procedure ASTM D-5169, approved Sep. 15, 1991 and published November 1991.

Each of the fastening components and elements in the various constructions of the invention may be operably attached to its supporting substrate by employing any one or more of the attachment mechanisms employed to construct and hold together the various other components of the article of the invention. The fastening elements in the various fastening regions, may be integrally formed, such as by molding, co-extrusion or the like, along with the associated substrate layer. The substrate layer and its associated mechanical fastening elements may be formed from substantially the same polymer material, and there need not be a discrete step of attaching the fastening elements to an initially separate substrate layer. For example, the individual hook elements may be integrally formed simultaneously with a hook base-layer by coextruding the base layer and hook elements from substantially the same polymer material.

It should be readily appreciated that the strength of the attachment or other interconnection between the substrate layer and the attached fastening component should be greater than the peak force required to remove the fastener tab 36 from its releasable securement to the appointed landing member of the article.

EXAMPLES

The following examples are presented to provide a more detailed understanding of the invention. The examples are representative, and are not intended to limit the scope of the invention.

Example 1

The extensible outercover of this example was composed of a 0.5 osy (17 g/m$^2$) polypropylene spunbond fabric which was necked 70%. The fabric was composed of PC-973 polypropylene obtained from Montell, USA, Inc., a business having offices in Wilmington, Del. 19850. The spunbond fibers were formed at the 0.5 osy (17 g/m$^2$) basis weight and thermally bonded with a wire weave bond pattern at a 12–17% bond area.

Figure 8:
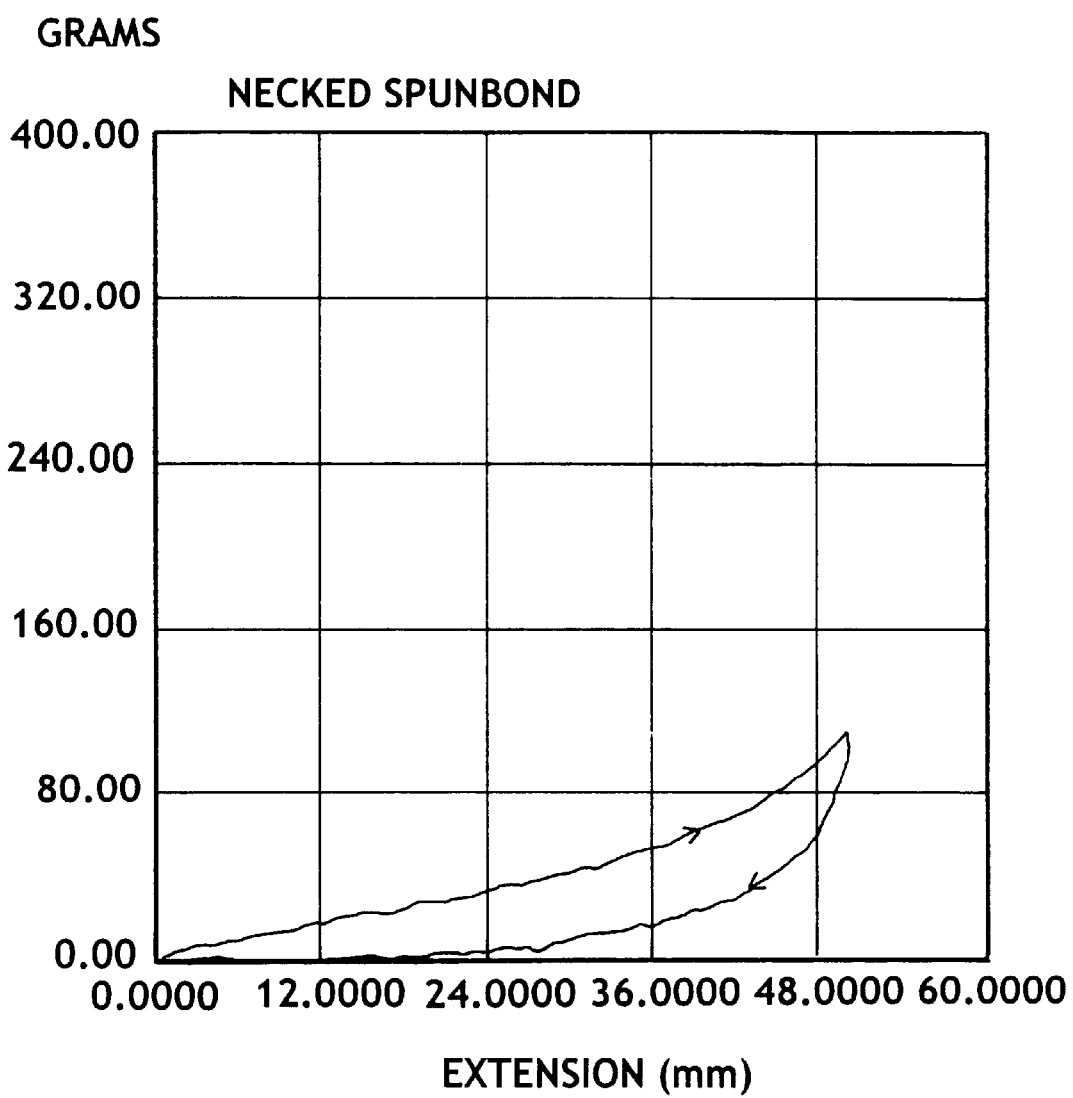

With reference to the upper part of the curve shown in FIG. 8, the extensible outer cover exhibits about 40 mm of extension under 60 grams of force for a two inches wide sample, which corresponds to about 40 mm of extension under 30 grams of force per inch of sample width. FIG. 8 also shows that the extensible outer cover exhibits about 18 mm of permanent deformation, as indicated by the 18 mm of remaining extension on the lower portion of the curve when the retraction force returns to zero. This is corresponds to about 24.5% of permanent deformation.

The substrate was composed of a 0.75 mil (0.019 mm) thick, green polyethylene film which was corona treated on both sides, and was nonelastomeric and substantially non-expandable. The film was produced from a resin Code XEM 244.0, and obtained from Huntsman Packaging Corp., a business having offices in Chippewa Falls, Wis. 54719.

The necked-spunbond extensible outercover was combined with the polyethylene film substrate by spraying a Findley H-2525 adhesive along the perimeter edge regions of the substrate employing a PAM 600 SPRAYMATIC adhesive applicator made by PAM Fastening Technology, Inc. of Charlotte, N.C. 28266. The outermost edges of the substrate measured 7 inches (178 mm) by 19 inches (483 mm) in length. The 0.5 osy (17 g/m$^2$), 70% necked, spunbond, extensible outercover was placed on top of the adhesive and arranged to be extensible along the 7-inch (178 mm) direction of the substrate. A rubber roller was used to apply pressure to attach the perimeter of the outercover material to the substrate.

The 7-inch (178 mm) dimension of the resulting composite was trimmed from 7 inches (178 mm) to a length of 5 inches (127 mm), and the resulting composite was cut into a plurality of 5 inch (127 mm)×2 inch (50.8 mm) strips for tensile testing. In the middle region of each sample strip, a 4 inch (102 mm) region of the necked spunbond was not attached to the polyethylene film substrate.

Figure 10:
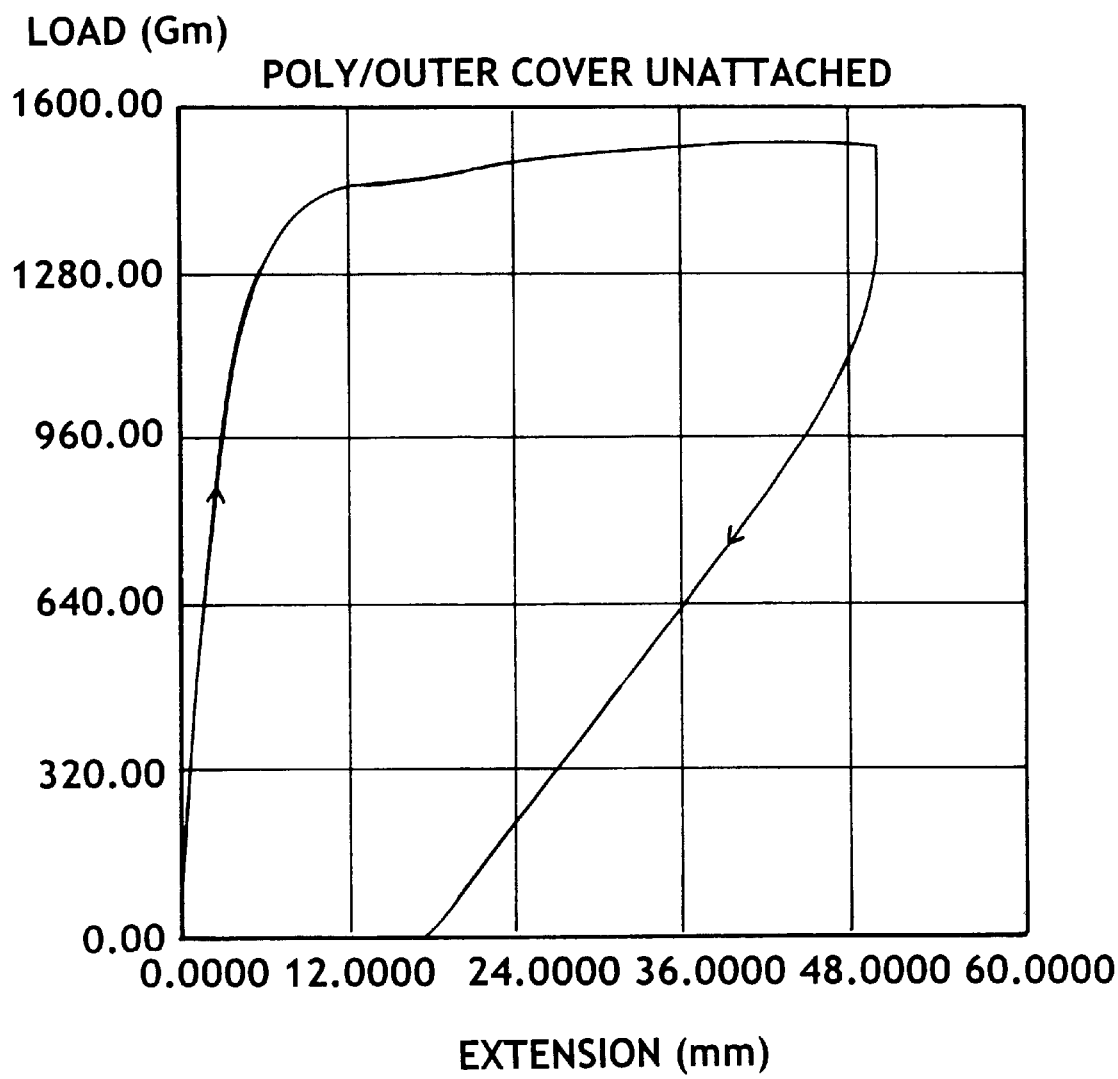
FIG. 10 shows a representative stress-strain curve provided by an extensible outercover layer which is substantially unattached to an adjacent substrate layer, in accordance FIG. 9.

The stress-strain properties of the combination are representatively shown in FIG. 10. When the extensible outercover is not attached to the non-expandable substrate, the stress-strain curve of the composite is similar to the stress-strain curve produced by the substrate alone. The behavior of the extensible outercover is substantially unaffected by the substrate, and the properties of the outercover remain similar to those illustrated in FIG. 8.

Example 2

In this example, an extensible outercover was assembled and operatively attached to a substrate composed of a substantially elastomeric material. The extensible outercover was composed of the necked spunbond fabric material employed for the extensible outercover of Example 1.

The substrate was composed of a standard metallocene, Necked-Bonded-Laminate (mNBL) composite. The composite included of two, necked non-woven facings composed of 0.5 osy (17 g/m$^2$, polypropylene spunbond fabric necked to 45%. A single, 35 g/m$^2$ film layer composed of metallocene DOW XU 58380 elastomer (obtained from Dow Chemical Company, a business with offices in Midland, Mich. 48674) was extruded onto one of the necked 0.5 osy (17 g/m$^2$) non-woven facings, and the second 0.5 osy (17 g/m$^2$) necked non-woven facing was attached to the opposite side of the elastomer film to create the non-woven/film/non-woven laminate. The mNBL had an extendibility and stretchability along the necked-gathering direction of the composite.

To provide the assembly of Example 2, a Findley H-2525 adhesive was sprayed over the entire surface of a mNBL substrate, which measured 7 inch (178 mm)×19 inch (483 mm), using the PAM 600 SPRAYMATIC adhesive applicator. The 7-inch (178 mm) dimension corresponded to the stretchable direction of the mNBL. The 0.5 osy (17 glm$^2$), 70% necked spun bond facing was placed on top of the adhesive and arranged to be extensible along the 7-inch (178 mm) dimension of the mNBL substrate. A rubber roller was used to apply pressure to attach the extensible outercover to the substrate.

Figure 10A:
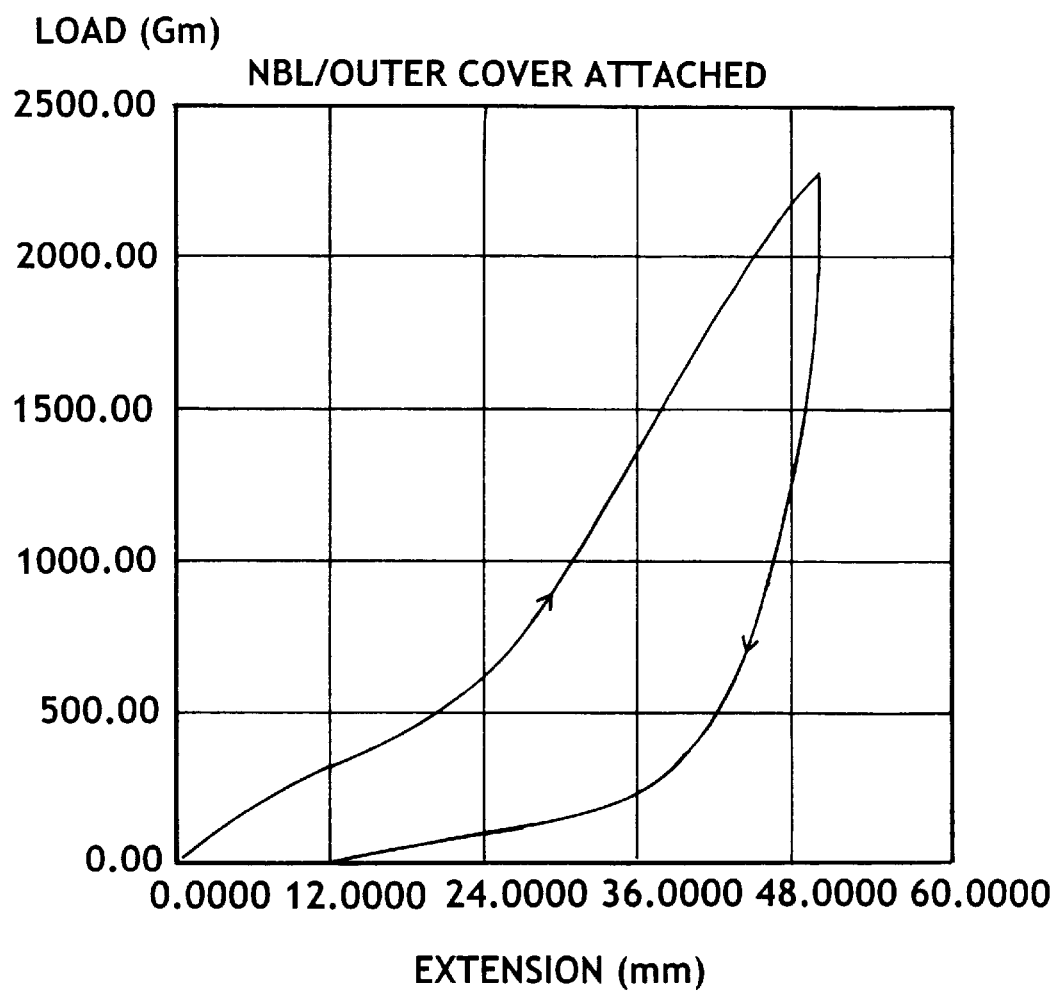
FIG. 10A shows a representative stress-strain curve provided by an extensible outercover layer which is attached to an elastomeric substrate layer in accordance FIG. 9A.

The stress-strain, mechanical properties of the assembly of this example are representatively shown in FIG. 10A. From FIG. 10A, it can be seen that the attachment of the expandable cover had a minimal impact on the behavior of the elastomeric substrate. The properties of the assembly substantially corresponded to the properties of the elastomeric substrate by itself. With reference to FIG. 10A, the force needed to extend the composite assembly in FIG. 10A was 1350 grams at an extension of 36 mm. With reference to FIG. 8, the force needed to extend the expandable cover to 36 mm was only 55 grams. During the unload cycle (lower portion) of the stress-strain curve in FIG.10A, the elastomeric substrate retracts the composite assembly with a large retractive force which provides a minimal permanent deformation. At 36 mm of elongation, the composite assembly of the Example 2 represented in FIG. 10A had a retractive force of 250 grams while the retractive force of the extensible outercover alone has a force of only 20 grams (FIG. 8). Similarly, the composite assembly of Example 2 exhibited less than 10 mm of permanent deformation while the expandable cover alone exhibited 30 mm of permanent deformation (FIG. 8).

Example 3

An extensible outercover was assembled and attached to a substantially substrate composed of a non-elastomeric and substantially non-extendible material. The extensible outercover was composed of the necked spunbond fabric material employed to construct the extensible outercover of Example 1, and the substrate was composed of the 0.75 mil (0.019 mm), green polyethylene film employed to construct the substrate of Example 1.

The composite assembly of Example 3 was constructed by spraying Findley H-2525 adhesive over the entire polyethylene film substrate, which measured 7 inch (178 mm)× 19 inch (483 mm), using the PAM 600 SPRAYMATIC adhesive applicator. The 0.5 osy (17 g/m$^2$), 70% necked, spunbond, extensible outercover was placed on top of the adhesive with the outercover arranged to be extensible along 7 inch (178 mm) dimension of the substrate. A rubber roller was used to apply pressure to attach the extensible outercover to the substrate.

Figure 10B:
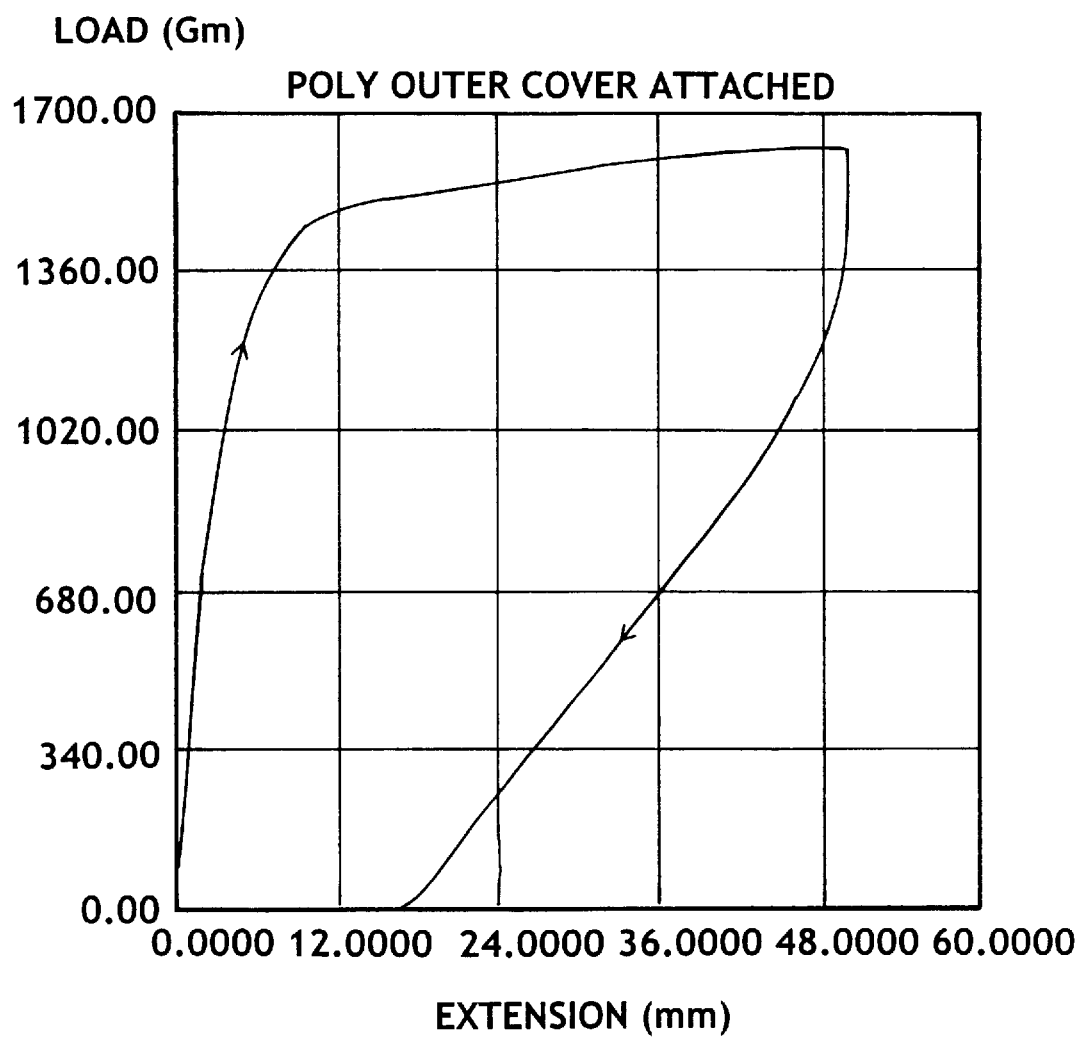
FIG. 10B shows a representative stress-strain curve provided by an extensible outercover layer which is attached to a non-elastomeric, substantially non-expandable substrate in accordance with FIG. 9B.

Comparing FIGS. 10A and 10B, it can be seen that the permanent deformation is larger for the assembly of Example 3 because of the substantially non-elastomeric substrate material. Comparing FIGS. 8 and 10B, it can be seen that, for the same amount of extension, the force required to stretch the assembly is much higher than that required to stretch the extensible outercover alone. As a result, the tensile load-extension properties of the assembly of Example 3 are very similar to those of Example 1. In addition, the assembly of an extensible outer cover uniformly attached to a non-extendible and nonelastomeric substrate no longer allows the outercover to exhibit its extensibility feature. Instead, the outercover is forced and constrained to exhibit the properties of the attached substrate. Thus, it can be seen that non-extensible zones may be selectively created by attaching appointed portions of the extensible outer cover to various predetermined substrates creating pre-selected areas or zones along the outercover which may be elastomeric, or may be nonelastomeric and substantially non-extendible.

It should be noted that in FIGS. 8 and 10 through 10B, the upper portion of the shown curve represents the load-extension behavior when the tested sample is under tension. The lower portion of the shown curve represents the load-extension behavior when the tested sample is under relaxation/retraction.

Example 4

A representative example of the invention provided a "size 3" or medium diaper for an infant weighting between 16–28 pounds (7.26–12.7 kg). The diaper has the configurations and shapes illustrated in FIGS. 3 through 4A.

The front body panel 53 measured 11 inches (279 mm) along the cross-direction and 4.5 inches (114 mm) along the longitudinal direction, and was composed of a 1.0 osy (34 g/m$^2$) polypropylene spunbond fabric. The back or rear body panel 52 measured 11 inches (279 mm) along the cross-direction and 5.75 inches (146 mm) along the longitudinal direction, and was composed of a necked-bonded-laminate material which had a basis weight of 77 gsm. and was laterally stretchable 20–40% in the cross-direction. The desired curvatures were formed along the medial portions of the inboard edges 64 and 65 of the front and back panels 52 and 53, respectively. Four, 0.25 inch (6.35 mm) wide strips of 3M-927, two-sided adhesive tape were applied to attach the expandable sections 90 of the absorbent composite to the front and back panels at the four side securement sections 42.

The absorbent body composite 32 included a substantially liquid-impervious backsheet layer 30 which measured 8 inches (203 mm) in the cross-direction and 14 inches (356 mm) in the longitudinal direction, and was composed of a 0.75 mil (0.019 mm) polyethylene film. A cellulose tissue wrap sheet 74 was overlaid onto and wrapped around a retention portion 48 that was composed of a mixture 63% cellulosic, woodpulp fluff and 37% superabsorbent polymer (FAVOR 880 from Stockhausen). The wrapped retention portion was debulked to a thickness of 0.2 inches (5.08 mm), and cut to an hour glass shape. The shaped retention portion measured 12 inches (305 mm) in the longitudinal direction, and had a cross-directional width of 4.0 inches (102 mm) at its two ends. The crotch region of the retention portion was narrowed to a width of 3.5 inches (89 mm). A layer of surge material 46 was adhesively attached to the front of the tissue wrap at a location spaced 2.0 inches (50.8 mm) from the front-most edge of the tissue edge. The surge layer had a basis weight of 2.5 osy (85 g/m$^2$) and a density of 0.024 g/cm$^3$. The surge layer measured 3 inches (76.2 mm) in the cross-direction and 6 inches (152 mm) in the longitudinal direction. A light spray of adhesive was applied to the backsheet layer to attach the backsheet layer to the tissue-wrapped retention portion. The front-most edge of the tissue wrapsheet was placed about 0.75 inches (19.1 mm) inboard from the leading, front-most edge of the backsheet layer, and a light spray of adhesive attached the top, bodyside surface of the surge layer 46 to the outward surface of the liquid-permeable topsheet layer 28. The topsheet was composed of a 0.5 osy (17 g/m$^2$) polypropylene spunbond fabric treated with 0.3% surfactant, and was placed over the surge layer 46, the wrapsheet 74 and the retention portion 48. The topsheet was adhesively bonded to the various absorbent components and to the perimeter of backsheet layer to create the assembled, absorbent body composite.

The side edge regions 80 of the topsheet and backsheet layers in the absorbent composite 32 were folded and tucked to create the z-folded pleats 92. The inward facing, topsheet portion of the z-folded pleat 92 was then attached to the outward-facing surfaces of the front and back panels with 0.25 inches (6.35 mm) wide strips of adhesive located at the four side securement sections 42. Accordingly the absorbent body composite 32 was assembled and joined to interconnect and bridge between the spaced-apart front body panel 53 and back body panel 52.

A very narrow width of spray adhesive was selectively applied down the center of the backsheet layer 30 of the absorbent composite 32. Also, the spray adhesive was applied to the exposed, outward, non-bodyside of the front and back body panels 52 and 53. Care was taken to not spray the adhesive over the z-folded pleats of the absorbent composite. A narrow width of adhesive was sprayed across the lateral ends of the absorbent composite thereby sealing the absorbent ends. A single piece of 60% necked polypropylene spunbond fabric at a basis weight of 1.2 g/m$^2$ was placed over the outward side of the pleated, attached absorbent composite, and over the outward side of the exposed body panels to provide the extensible outercover layer 40. The necked spunbond fabric was attached at the sprayed adhesive zones, and a rotary cutter was used to cut out the excess material to the shape of the garment.

Each leg elastic member 34 included two, 940 dtx (decitex) elastomeric strands 98 composed of LYCRA XA SPANDEX elastomer. The elastomeric strands were elongated to 300% elongation and adhesively laminated to a 0.4 osy (13.6 g/m$^2$) polypropylene facing member with a FIND-LEY H2525A adhesive. The leg elastic members were stretched-to-stop, and ultrasonically point bonded to the side marginal edges of the backsheet 30. In particular, the elastic members were located on the outward facing surface of the backsheet layer and positioned within a fold-region of the z-folded pleat 92. Longitudinal end portions of each leg elastic member 34 were angled outboard to extend laterally beyond the side edge regions 80 of the absorbent composite, and were attached to the front and back body panels. Accordingly, the laterally opposed pair of leg elastic members 34 created a gathered element at each leg opening of the diaper.

Mechanical, hook-type fastener tabs 36 were adhesively and ultrasonically attached to the ear portions 38 of the back body panel 52 of the diaper. Preferably, the longitudinally terminal edges of the fastener tabs were substantially aligned with the end edge 60 of the back body panel 52 at the waist band side edge regions 86.

Having described the invention in rather full detail, It will be readily apparent that various changes and modifications can be made without departing from the spirit of the invention. All of such changes and modifications are contemplated as being within the scope of the invention as defined by the subjoined claims.

We claim:

1. An integral absorbent article having a longitudinal article length and a lateral article width, said article comprising:
    an absorbent composite having a first end region, a second end region which is longitudinally opposed from said first end region, laterally opposed side regions, a bodyside surface, an outward surface, and a first longitudinally terminal end edge, said absorbent composite further including
        a substantially liquid-impermeable backsheet layer,
        a liquid permeable topsheet layer, and
        a retention portion sandwiched between said backsheet and topsheet layers;
    a separately provided, first body panel having
    a bodyside surface,
    an outward surface,
    a panel length which is less than said article length,
    an outboard terminal end edge, and
    a relatively inboard terminal end edge;
    an expandable attachment section joined along at least a portion of each side region of said absorbent composite in said first end region of the absorbent composite, each expandable attachment section extendible in length at least outwardly, and each expandable attachment section configured to secure its correspondingly joined side edge region of the absorbent composite to said outward surface of said first body panel; and
    a substantially non-elastomeric, extensible outercover joined to extend over a major portion of said outward surface of said absorbent composite, said substantially non-elastomeric, extensible outercover capable of providing a sustained deformation when subjected to a tensile force and then allowed to relax after a removal of said tensile force, wherein said extensible outercover provides an elongation of at least about 1 cm when subjected to a tensile force of 30 gmf per inch, and said extensible outercover provides a sustained deformation of at least about 20% when subjected to a tensile force of 50 gmf per inch and then allowed to relax, after the removal of said tensile force, for a period of 1 minute.

2. An absorbent article as recited in claim 1, further comprising:
    a separately provided, second body panel having a bodyside surface, an outward surface, a panel length which is less than said article length, a second longitudinally outboard terminal end edge, and a relatively inboard, longitudinally terminal end edge;
    wherein said outward surface of said second body panel is joined to said absorbent composite.

3. An absorbent article as recited in claim 2, further comprising:
    an expandable attachment section joined along at least a portion of each side region of the absorbent composite in said second end region of the absorbent composite, wherein each expandable attachment section is expandable at least along a cross-direction of said article, and each expandable attachment section is configured to secure its correspondingly joined side edge region of said second end region of the absorbent composite to said outward surface of said second body panel.

4. An absorbent article as recited in claim 2, wherein said second body panel has a longitudinal length which is at least about 15% of said article length and not more than about 40% of said article length.

5. An absorbent article as recited in claim 2, wherein said second body panel is longitudinally spaced from said first body panel.

6. An absorbent article as recited in claim 1, wherein said first longitudinally terminal end edge of said absorbent composite is substantially coterminous with said article.

7. An absorbent article as recited in claim 1, wherein said relatively inboard, longitudinally terminal end edge of said first body panel has a medial portion, and at least said medial portion of said relatively inboard, longitudinally terminal end edge of said first body panel is substantially unattached to said absorbent composite.

8. An absorbent article as recited in claim 1, wherein said first longitudinally terminal end edge of said absorbent composite is spaced relatively inboard from said first longitudinally outboard terminal end edge of said first body panel.

9. An absorbent article as recited in claim 1, wherein said expandable attachment section includes at least one substantially z-folded pleat member.

10. An absorbent article as recited in claim 1, wherein said expandable attachment section includes at least one z-folded pleat portion of said each side region of the absorbent composite.

11. An absorbent article as recited in claim 1, wherein said expandable attachment section includes a plurality of micro-pleats.

12. An absorbent article as recited in claim 1, wherein said expandable attachment section includes an elastomeric material.

13. An absorbent article as recited in claim 1, wherein said backsheet layer includes an elastomeric material, each laterally opposed side region of said absorbent composite includes a corresponding, laterally opposed side region of said backsheet layer, and each said expandable attachment section includes a portion of its corresponding laterally opposed side region of said backsheet layer.

14. An absorbent article as recited in claim 1, wherein said expandable attachment section can provide a transverse elongation of at least about 1 cm under a tensile force of 12 gmf per centimeter of cross-wise length of the expandable attachment section.

15. An absorbent article as recited in claim 1, wherein said article includes a first laterally extending end seal which is provided along at least a portion of said first end of the absorbent composite to resist a passage of liquid between said absorbent composite and said outward surface of said first body panel.

16. An absorbent article as recited in claim 1, wherein said first body panel has a longitudinal length which is at least about 5% of said article length.

17. An absorbent article as recited in claim 1, wherein said first body panel has a longitudinal length which is not more than about 40% of said article length.

18. An absorbent article as recited in claim 1, wherein said article further includes a substantially non-extensible component which is affixed to said extensible outercover to provide a substantially non-extensible region in said outercover.

19. An absorbent article as recited in claim 1, wherein said article further includes an elastomeric component which is affixed to said extensible outercover to provide an elastomeric region in said outercover.

20. An integral absorbent article having a longitudinal article length and a lateral article width, said article comprising:
   an absorbent composite having a first end region, a second end region which is longitudinally opposed from said first end region, laterally opposed side regions, a bodyside surface, an outward surface, and a first longitudinally terminal end edge, said absorbent composite further including
      a substantially liquid-impermeable backsheet layer,
      a liquid permeable topsheet layer, and
      a retention portion sandwiched between said backsheet and topsheet layers;
   a separately provided, first body panel having
      a bodyside surface,
      an outward surface,
      a panel length which is less than said article length,
      an outboard terminal end edge,
      a relatively inboard terminal end edge, and
      laterally opposed end sections that extend laterally beyond said backsheet layer;
   an expandable attachment section joined along at least a portion of each side region of said absorbent composite in said first end region of the absorbent composite, each expandable attachment section extendible in length at least outwardly, and each expandable attachment section configured to secure its correspondingly joined side edge region of the absorbent composite to said outward surface of said first body panel; and
   an extensible outercover joined to extend over a major portion of said outward surface of said absorbent composite; wherein
   said extensible outercover provides an elongation of at least about 1 cm when subjected to a tensile force of 30 gmf per inch, and
   said extensible outercover provides a sustained deformation of at least about 20% when subjected to a tensile force of 50 gmf per inch and then allowed to relax, after a removal of said tensile force, for a period of 1 minute.

21. An article as recited in claim 20, wherein first body panel includes laterally opposed end sections that extend laterally beyond side edges of said absorbent composite to provide ear sections of said article.

22. An integral absorbent article having a longitudinal article length and a lateral article width, said article comprising:
   an absorbent composite having a first end region, a second end region which is longitudinally opposed from said first end region, laterally opposed side regions, a bodyside surface, an outward surface, and a first longitudinally terminal end edge, said absorbent composite further including
      a substantially liquid-impermeable backsheet layer,
      a liquid permeable topsheet layer, and
      a retention portion sandwiched between said backsheet and topsheet layers;
   an extensible outercover joined to extend over a major portion of said outward surface of said absorbent composite, said extensible outercover capable of providing a sustained deformation when subjected to a tensible force and then allowed to relax after a removal of said tensible force;
   a first body panel having a bodyside surface, an outward surface, a panel length which is less than said article length, a first longtudinally outboard terminal end edge, and a relatively inboard, longtudinally terminal end edge; and
   an expendable attachment section joined along at least a portion of each region of the absorbent composite in said first end region of the absorbent composite; wherein
      each expandable attachment section is expandable at least along a cross-section of said article,
      each expandable attachment section is configured to secure its correspondingly joined side edge region of the absorbent composite to said outward surface of said first body panel, and
      and each expandable attachment section includes at least one substantially z-folded pleat member.

23. An integral absorbent article having a longitudinal article length and a lateral article width, said article comprising:
   an absorbent composite having a first end region, a second end region which is longitudinally opposed from said first end region, laterally opposed side regions, a bodyside surface, an outward surface, and a first longitudinally terminal end edge, said absorbent composite further including
      a substantially liquid-impermeable backsheet layer,
      a liquid permeable topsheet layer, and
      a retention portion sandwiched between said backsheet and topsheet layers;
   an extensible outercover joined to extend over a major portion of said outward surface of said absorbent composite, said extensible outercover capable of providing a sustained deformation when subjected to a tensile force and then allowed to relax after a removal of said tensile force;
   a first body panel having a bodyside surface, an outward surface, a panel length which is less than said article length, a first longitudinally outboard terminal end edge, and a relatively inboard, longitudinally terminal end edge; and an expandable attachment section joined along at least a portion of each side region of the absorbent composite in said first end region of the absorbent composite; wherein each expandable attachment section is expandable at least along a cross-direction of said article, each expandable attachment section is configured to secure its correspondingly joined side edge region of the absorbent composite to said outward surface of said first body panel, and each expandable attachment section includes a plurality of micro-pleats.

24. An integral absorbent article having a longitudinal article length and a lateral article width, said article comprising:

an absorbent composite having a first end region, a second end region which is longitudinally opposed from said first end region, laterally opposed side regions, a bodyside surface, an outward surface, and a first longitudinally terminal end edge, said absorbent composite further including a substantially liquid-impermeable backsheet layer, a liquid permeable topsheet layer, and a retention portion sandwiched between said backsheet and topsheet layers;

an extensible outercover joined to extend over a major portion of said outward surface of said absorbent composite, said extensible outercover capable of providing a sustained deformation when subjected to a tensile force and then allowed to relax after a removal of said tensile force; and a separately provided, first body panel having a bodyside surface, an outward surface, a panel length which is less than said article length, a first longitudinally outboard terminal end edge, a relatively inboard, longitudinally terminal end edge, and laterally opposed end sections that extend laterally beyond side edges of said backsheet layer and extend laterally beyond side edges of said absorbent composite to provide ear sections of said article; wherein said absorbent composite is joined to said outward surface of said first body panel, said relatively inboard, longitudinally terminal end edge of said first body panel has a medial portion, and at least said medial portion of said relatively inboard, longitudinally terminal end edge of said first body panel is substantially unattached to said absorbent composite.

25. An integral absorbent article having a longitudinal article length and a lateral article width, said article comprising:

an absorbent composite having a first end region, a second end region which is longitudinally opposed from said first end region, laterally opposed side regions, a bodyside surface, an outward surface, and a first longitudinally terminal end edge, said absorbent composite further including a substantially liquid-impermeable backsheet layer, a liquid permeable topsheet layer, and a retention portion sandwiched between said backsheet and topsheet layers;

an extensible outercover joined to extend over a major portion of said outward surface of said absorbent composite, said extensible outercover capable of providing a sustained deformation when subjected to a tensile force and then allowed to relax after a removal of said tensile force;

a separately provided, first body panel having a bodyside surface, an outward surface, a panel length which is less than said article length, a first longitudinally outboard terminal end edge, a relatively inboard, longitudinally terminal end edge, and laterally opposed end sections that extend laterally beyond side edges of said backsheet layer; and an expandable attachment section joined along at least a portion of each side region of the absorbent composite in said first end region of the absorbent composite; wherein each expandable attachment section is expandable at least along a cross-section of said article, each expandable attachment section is configured to secure its correspondingly joined side edge region of the absorbent composite to said outward surface of said first body panel, and each expandable attachment section can provide a transverse elongation of at least 1 cm under a tensile force of 12 gmf per centimeter of cross-wise length of the expandable attachment section.

26. An article as recited in claim 25, wherein first body panel includes laterally opposed end sections that extend laterally beyond side edges of said absorbent composite to provide ear sections of said article.

* * * * *